(12) United States Patent
Sapir

(10) Patent No.: US 11,324,549 B2
(45) Date of Patent: May 10, 2022

(54) INTERATRIAL SEPTUM PENETRATION

(71) Applicant: TRANSSEPTAL SOLUTIONS LTD., Kefar Monash (IL)

(72) Inventor: Elad Sapir, Kefar Vitkin (IL)

(73) Assignee: TRANSSEPTAL SOLUTIONS LTD., Kefar Monash (IL)

( * ) Notice: Subject to any disclaimer, the term of this patent is extended or adjusted under 35 U.S.C. 154(b) by 1226 days.

(21) Appl. No.: 15/649,110

(22) Filed: Jul. 13, 2017

(65) Prior Publication Data

US 2017/0303961 A1 Oct. 26, 2017

Related U.S. Application Data

(63) Continuation of application No. 14/882,687, filed on Oct. 14, 2015, now Pat. No. 10,398,503.

(51) Int. Cl.
*A61B 18/14* (2006.01)
*A61B 17/34* (2006.01)
(Continued)

(52) U.S. Cl.
CPC ...... *A61B 18/1492* (2013.01); *A61B 17/3478* (2013.01); *A61B 18/1477* (2013.01);
(Continued)

(58) Field of Classification Search
CPC ............ A61B 18/1492; A61B 18/1477; A61B 2018/00577; A61B 2017/00247; A61M 2025/0095; A61M 25/0606
See application file for complete search history.

(56) References Cited

U.S. PATENT DOCUMENTS 4,677,990 A 7/1987 Neubauer
5,010,892 A 4/1991 Colvin et al.
(Continued)

FOREIGN PATENT DOCUMENTS

DE 102005023414 11/2006
EP 0808607 11/1997
(Continued)

OTHER PUBLICATIONS

An International Search Report and a Written Opinion both dated Sep. 30, 2014, which issued during the prosecution of Applicant's PCT/IL2014/050338.
(Continued)

*Primary Examiner* — Michael F Peffley
*Assistant Examiner* — Samantha M Good
(74) *Attorney, Agent, or Firm* — Sughrue Mion, PLLC

(57) ABSTRACT

A method is provided, including inserting a catheter into a right atrium of a heart of the subject. A distal portion of the catheter is advanced toward a fossa ovalis of the heart. A flexible longitudinal member is deployed from the catheter, such that a deployed portion of the flexible longitudinal member is loop-shaped. The fossa ovalis is contacted with the deployed portion of the flexible longitudinal member. A needle is deployed from the catheter. A distal end of the needle is brought in contact with a site on a surface of an interatrial septum of the heart outside the fossa ovalis. A hole is formed through the interatrial septum at the site with the needle. The deployed portion of the flexible longitudinal member is withdrawn toward the catheter.

11 Claims, 19 Drawing Sheets

(51) Int. Cl.
  *A61B 17/00* (2006.01)
  *A61B 90/00* (2016.01)
  *A61B 18/00* (2006.01)
  *A61M 25/06* (2006.01)
  *A61M 25/00* (2006.01)

(52) U.S. Cl.
  CPC .............. *A61B 2017/003* (2013.01); *A61B 2017/00247* (2013.01); *A61B 2017/00867* (2013.01); *A61B 2018/00577* (2013.01); *A61B 2090/034* (2016.02); *A61B 2090/065* (2016.02); *A61B 2090/3966* (2016.02); *A61M 25/0606* (2013.01); *A61M 2025/0095* (2013.01)

(56) References Cited

U.S. PATENT DOCUMENTS

| | | |
|---|---|---|
| 5,042,161 A | 8/1991 | Hodge |
| 5,069,674 A | 12/1991 | Fearnot et al. |
| 5,329,923 A | 7/1994 | Lundquist |
| 5,423,773 A | 6/1995 | Jimenez |
| 5,489,296 A | 2/1996 | Love et al. |
| 5,497,774 A | 3/1996 | Swartz |
| 5,507,743 A | 4/1996 | Edwards |
| 5,571,215 A | 11/1996 | Sterman et al. |
| 5,573,520 A | 11/1996 | Schwartz et al. |
| 5,605,543 A | 2/1997 | Swanson |
| 5,639,276 A | 6/1997 | Weinstock et al. |
| 5,741,429 A | 4/1998 | Donadio et al. |
| 5,807,395 A | 9/1998 | Mulier et al. |
| 5,865,791 A | 2/1999 | Whayne et al. |
| 5,885,228 A | 3/1999 | Rosenman et al. |
| 5,910,150 A | 6/1999 | Saadat |
| 6,033,359 A | 3/2000 | Doi |
| 6,102,926 A | 8/2000 | Tartaglia |
| 6,517,550 B1 | 2/2003 | Konya et al. |
| 6,575,921 B2 | 6/2003 | Vanden Hoek et al. |
| 6,623,448 B2 | 9/2003 | Slater |
| 6,623,449 B2 | 9/2003 | Paskar |
| 6,629,534 B1 | 10/2003 | St. Goar et al. |
| 6,641,564 B1 | 11/2003 | Kraus |
| 6,650,923 B1 | 11/2003 | Lesh |
| 6,761,708 B1 | 7/2004 | Chiu et al. |
| 6,796,963 B2 | 9/2004 | Carpenter et al. |
| 6,863,677 B2 | 3/2005 | Breznock |
| 7,048,733 B2 | 5/2006 | Hartley |
| 7,279,003 B2 | 10/2007 | Berra et al. |
| 7,344,543 B2 | 3/2008 | Sra |
| 7,581,328 B2 | 9/2009 | Greenhalgh et al. |
| 7,615,014 B2 | 11/2009 | Omata et al. |
| 7,635,353 B2 | 12/2009 | Gurusamy |
| 7,641,638 B2 | 1/2010 | Waxman et al. |
| 7,654,970 B2 | 2/2010 | Dubey et al. |
| 7,666,203 B2 | 2/2010 | Chanduszko |
| 7,708,704 B2 | 5/2010 | Mitelberg et al. |
| 7,815,577 B2 | 10/2010 | Krishnan |
| 7,824,341 B2 | 11/2010 | Krishnan |
| 7,850,644 B2 | 12/2010 | Gonzalez |
| 7,976,551 B1 | 7/2011 | Gutfinger |
| 8,000,809 B2 | 8/2011 | Elencwajg |
| 8,012,106 B2 | 9/2011 | Mangiardi et al. |
| 8,019,404 B2 | 9/2011 | Kapadia |
| 8,029,470 B2 | 10/2011 | Whiting et al. |
| 8,114,110 B2 | 2/2012 | Bednarek |
| 8,172,757 B2 | 5/2012 | Jaffe |
| 8,235,986 B2 | 8/2012 | Kulesa |
| 8,251,963 B2 | 8/2012 | Chin et al. |
| 8,292,910 B2 | 10/2012 | Chanduszko et al. |
| 8,317,810 B2 | 11/2012 | Stangenes |
| 8,353,898 B2 | 1/2013 | Lutze et al. |
| 8,491,619 B2 | 7/2013 | Breznock |
| 8,663,168 B2 | 3/2014 | Chin et al. |
| 8,694,077 B2 | 4/2014 | Kapadia |
| 8,747,459 B2 | 6/2014 | Nguyen et al. |
| 8,771,297 B2 | 7/2014 | Millet et al. |
| 8,911,384 B2 | 12/2014 | Santiago |
| 8,961,550 B2 | 2/2015 | Lenker et al. |
| 9,005,139 B2 | 4/2015 | Klaiman et al. |
| 9,339,230 B2 | 5/2016 | Kassab |
| 9,345,574 B2 | 5/2016 | Conklin |
| 9,545,265 B2 | 1/2017 | Maisano et al. |
| 9,668,674 B2 | 6/2017 | Sapir |
| 2002/0026175 A1 | 2/2002 | Paskar |
| 2002/0038129 A1 | 3/2002 | Peters et al. |
| 2002/0058960 A1 | 5/2002 | Hudson et al. |
| 2002/0143291 A1 | 10/2002 | Slater |
| 2002/0169377 A1 | 11/2002 | Khairkhahan |
| 2003/0125709 A1 | 7/2003 | Eidenschink |
| 2003/0144657 A1 | 7/2003 | Bowe |
| 2003/0191523 A1 | 10/2003 | Hojeibane |
| 2004/0220471 A1 | 11/2004 | Schwartz |
| 2004/0225304 A1 | 11/2004 | Vidlund et al. |
| 2005/0101984 A1 | 5/2005 | Chanduszko et al. |
| 2005/0149097 A1 | 7/2005 | Regnell |
| 2005/0149115 A1 | 7/2005 | Roue et al. |
| 2005/0177132 A1 | 8/2005 | Lentz et al. |
| 2005/0197623 A1 | 9/2005 | Leeflang et al. |
| 2005/0216018 A1 | 9/2005 | Sennett |
| 2006/0064062 A1 | 3/2006 | Gurusamy et al. |
| 2006/0074398 A1 | 4/2006 | Whiting et al. |
| 2006/0142756 A1* | 6/2006 | Davies ............... A61B 18/1492 606/45 |
| 2006/0241564 A1 | 10/2006 | Corcoran et al. |
| 2006/0241583 A1* | 10/2006 | Malecki ............ A61B 18/1492 606/41 |
| 2006/0276710 A1 | 12/2006 | Krishnan |
| 2007/0270741 A1 | 11/2007 | Hassett |
| 2008/0021405 A1 | 1/2008 | Jacobsen et al. |
| 2008/0097398 A1 | 4/2008 | Mitelberg et al. |
| 2008/0140173 A1 | 6/2008 | Eskaros et al. |
| 2008/0161840 A1 | 7/2008 | Osiroff |
| 2008/0188928 A1 | 8/2008 | Salahieh et al. |
| 2008/0243183 A1* | 10/2008 | Miller .................. A61M 25/10 606/228 |
| 2009/0171276 A1 | 7/2009 | Bednarek et al. |
| 2009/0312755 A1 | 12/2009 | Thapliyal et al. |
| 2010/0022948 A1 | 1/2010 | Wilson |
| 2010/0042110 A1 | 2/2010 | Kelley et al. |
| 2010/0168777 A1 | 7/2010 | Stangenes |
| 2010/0228276 A1 | 9/2010 | Breznock |
| 2011/0054487 A1 | 3/2011 | Farnan |
| 2011/0082538 A1 | 4/2011 | Dahlgren et al. |
| 2011/0251594 A1 | 10/2011 | Godin |
| 2011/0270239 A1 | 11/2011 | Werneth |
| 2011/0295107 A1 | 12/2011 | Kargar et al. |
| 2011/0313283 A1* | 12/2011 | Kapadia ............ A61B 17/3478 600/424 |
| 2012/0010503 A1 | 1/2012 | Mangiardi |
| 2012/0022427 A1 | 1/2012 | Kapadia |
| 2012/0065597 A1 | 3/2012 | Cohen |
| 2012/0179188 A1 | 7/2012 | Chanduszko |
| 2012/0277730 A1 | 11/2012 | Salahieh et al. |
| 2013/0041373 A1 | 2/2013 | Laufer |
| 2013/0123620 A1 | 5/2013 | Tekulve |
| 2013/0274784 A1 | 10/2013 | Lenker |
| 2014/0081302 A1 | 3/2014 | Thapliyal et al. |
| 2014/0081305 A1 | 3/2014 | Breznock et al. |
| 2014/0277054 A1 | 9/2014 | McNamara et al. |
| 2014/0309675 A1 | 10/2014 | Maisano et al. |
| 2014/0309678 A1 | 10/2014 | Maisano et al. |
| 2014/0309679 A1 | 10/2014 | Maisano et al. |
| 2014/0343538 A1 | 11/2014 | Lenker et al. |
| 2015/0173592 A1 | 6/2015 | Leeflang et al. |
| 2016/0015513 A1 | 1/2016 | Lashinski et al. |
| 2016/0100859 A1 | 4/2016 | Sapir et al. |
| 2016/0100860 A1 | 4/2016 | Lenker et al. |
| 2016/0256075 A1 | 9/2016 | Sapir |

(56) References Cited

U.S. PATENT DOCUMENTS

| | | |
|---|---|---|
| 2016/0374656 A1 | 12/2016 | Sapir |
| 2017/0105761 A1 | 4/2017 | Sapir et al. |

FOREIGN PATENT DOCUMENTS

| | | |
|---|---|---|
| WO | 95/08362 | 3/1995 |
| WO | 2011/130456 | 10/2011 |
| WO | 2013/128461 | 9/2013 |
| WO | 2014/064694 | 5/2014 |
| WO | 2014/170890 | 10/2014 |
| WO | 2016/059638 | 4/2016 |

OTHER PUBLICATIONS

U.S. Appl. No. 61/811,947, filed Apr. 15, 2013.
An Office Action dated Sep. 9, 2015, which issued during the prosecution of U.S. Appl. No. 14/245,135.
An Office Action dated Feb. 9, 2016, which issued during the prosecution of U.S. Appl. No. 14/245,135.
An Office Action dated Jan. 21, 2016, which issued during the prosecution of U.S. Appl. No. 14/287,523.
An Office Action dated Jan. 22, 2016, which issued during the prosecution of U.S. Appl. No. 14/287,470.
U.S. Appl. No. 62/095,150, filed Dec. 22, 2014.
An International Preliminary Report on Patentability dated Oct. 20, 2015, which issued during the prosecution of Applicant's PCT/IL2014/050338.
An Invitation to pay additional fees dated Jan. 15, 2016, which issued during the prosecution of Applicant's PCT/IL2015/051026.
An International Search Report and a Written Opinion both dated Mar. 30, 2016, which issued during the prosecution of Applicant's PCT/IL2015/051026.
An Office Action dated Aug. 23, 2016, which issued during the prosecution of U.S. Appl. No. 14/513,435.
An Office Action dated Jul. 21, 2016, which issued during the prosecution of U.S. Appl. No. 14/287,523.
Notice of Allowance dated Sep. 15, 2016, which issued during the prosecution of U.S. Appl. No. 14/287,470.
An Office Action dated Sep. 28, 2016, which issued during the prosecution of U.S. Appl. No. 14/636,759.
An Office Action dated Oct. 21, 2016, which issued during the prosecution of U.S. Appl. No. 14/245,135.
An Office Action dated Apr. 12, 2017, which issued during the prosecution of U.S. Appl. No. 14/287,523.
An Office Action dated Feb. 23, 2017, which issued during the prosecution of U.S. Appl. No. 14/513,435.
An Office Action dated Mar. 3, 2017, which issued during the prosecution of U.S. Appl. No. 15/258,210.
Notice of Allowance dated May 19, 2017, which issued during the prosecution of U.S. Appl. No. 14/245,135.
Notice of Allowance dated May 26, 2017, which issued during the prosecution of U.S. Appl. No. 15/258,210.
An Advisory Action dated Feb. 7, 2017, which issued during the prosecution of U.S. Appl. No. 14/245,135.
HHS Tube—Fort Wayne Metals—downloaded from http://www.fwmetals.com/products/hhs-tube/ Jan. 8, 2017—this product was commercially available sufficiently earlier than the effective U.S. filing date and any foreign priority date of the present application.
An Office Action dated Sep. 11, 2018, which issued during the prosecution of U.S. Appl. No. 15/619,626.
An Office Action dated Aug. 16. 2019, which issued during the prosecution of U.S. Appl. No. 15/702,106.
An English translation of an Office Action dated Aug. 21, 2019 which issued during the prosecution of Chinese Patent Application No. 201580067597.4.
A Non-Final Office Action issued in U.S. Appl. No. 16/262,280, dated Jan. 22, 2021.

\* cited by examiner

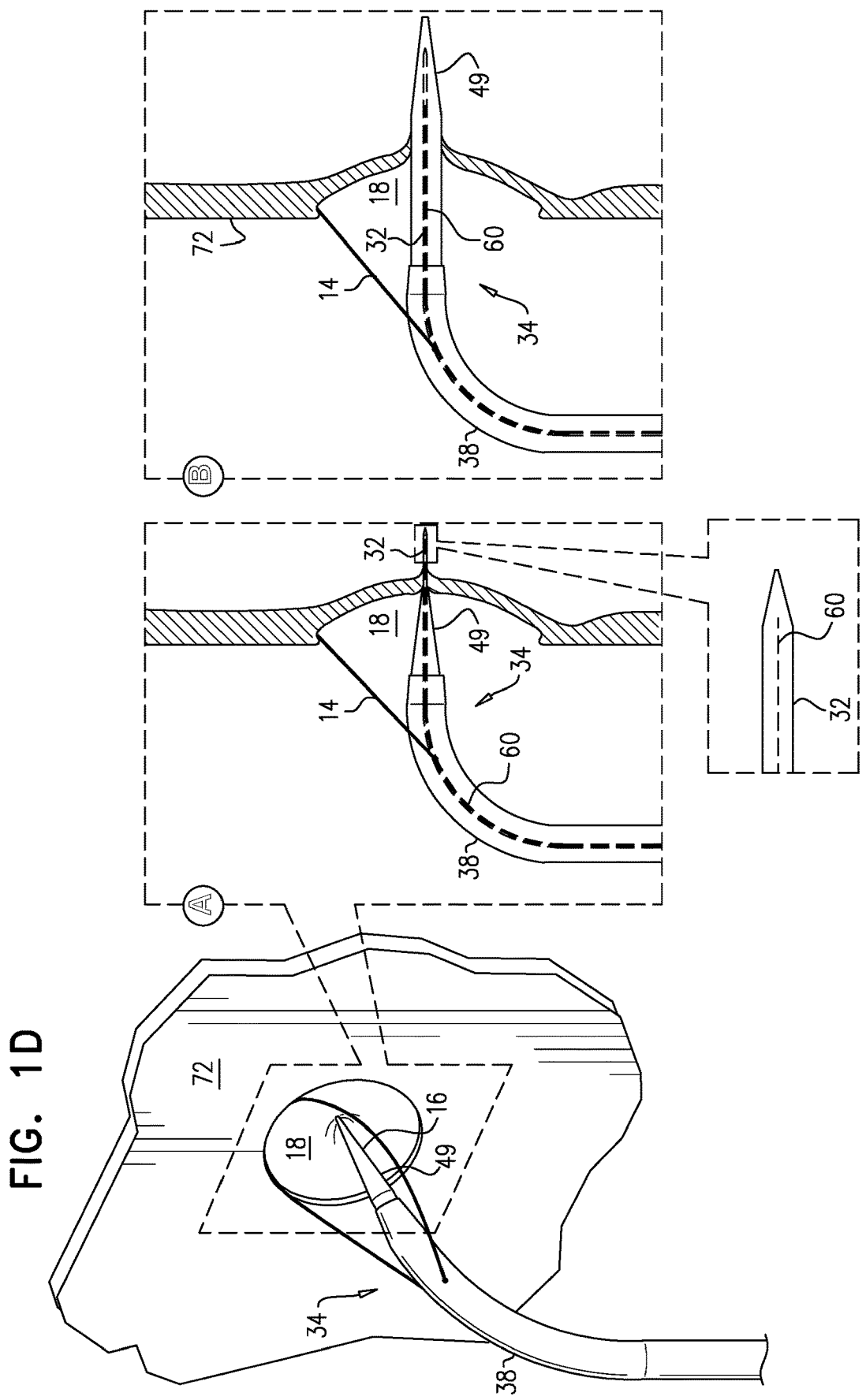

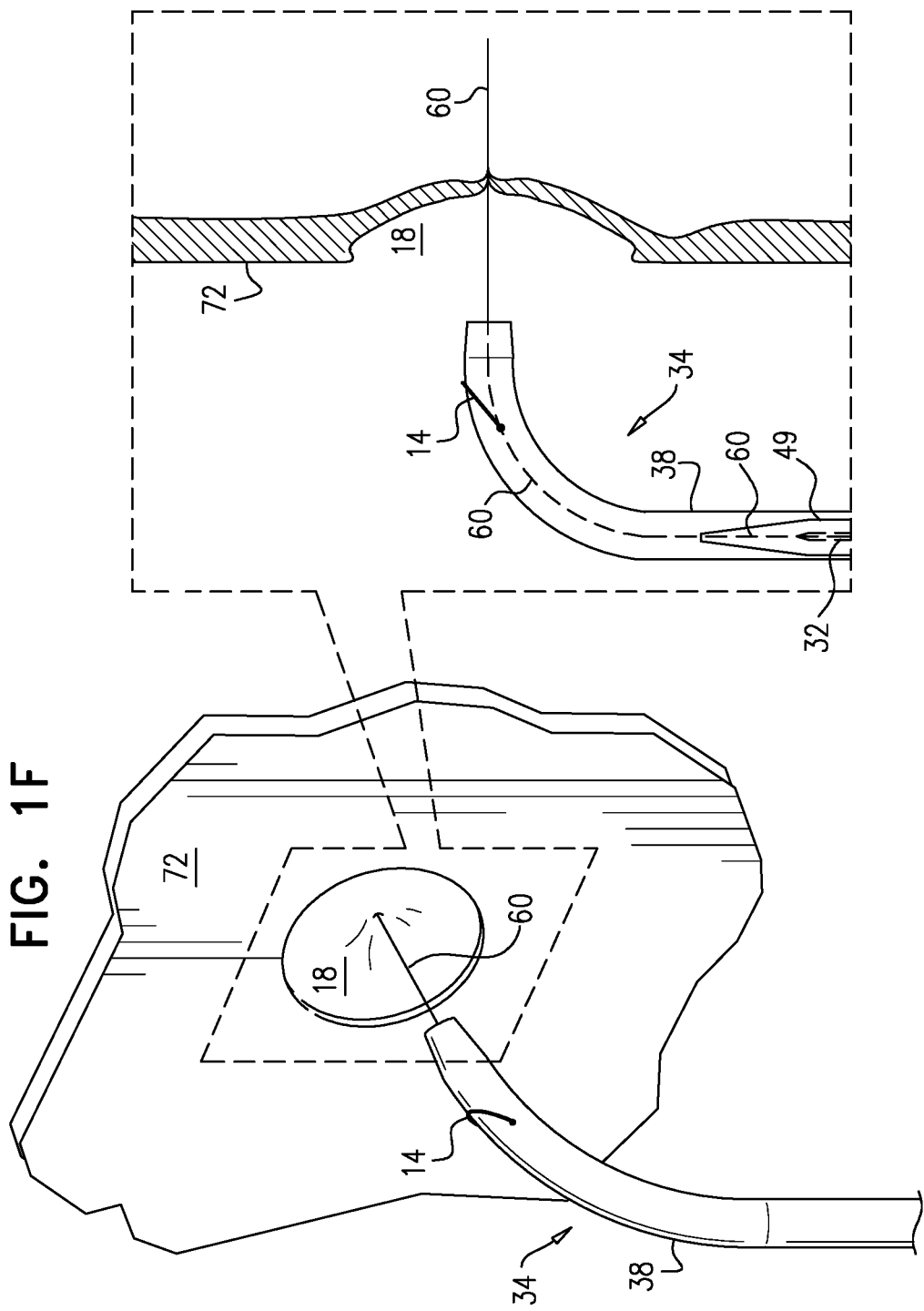

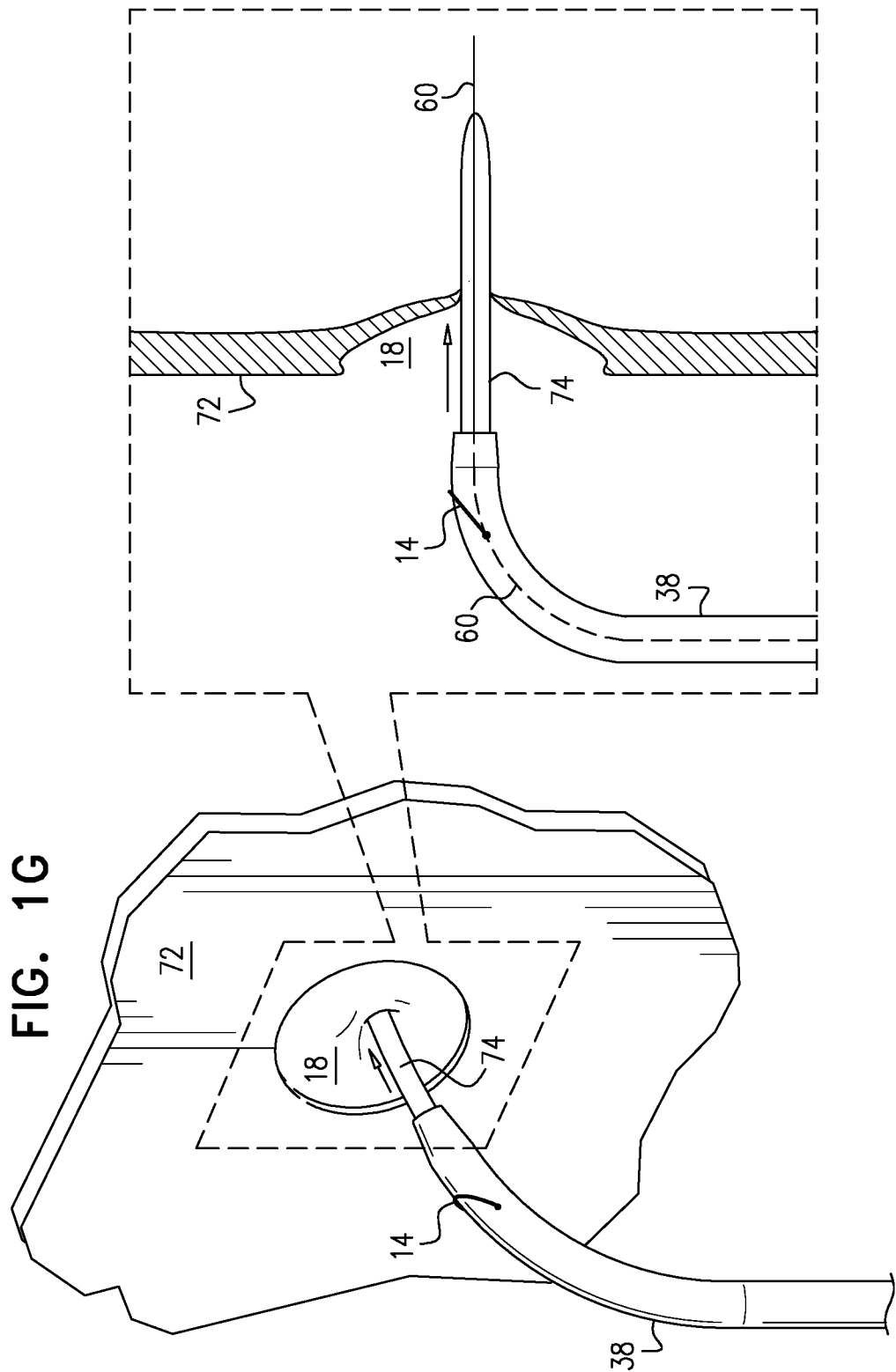

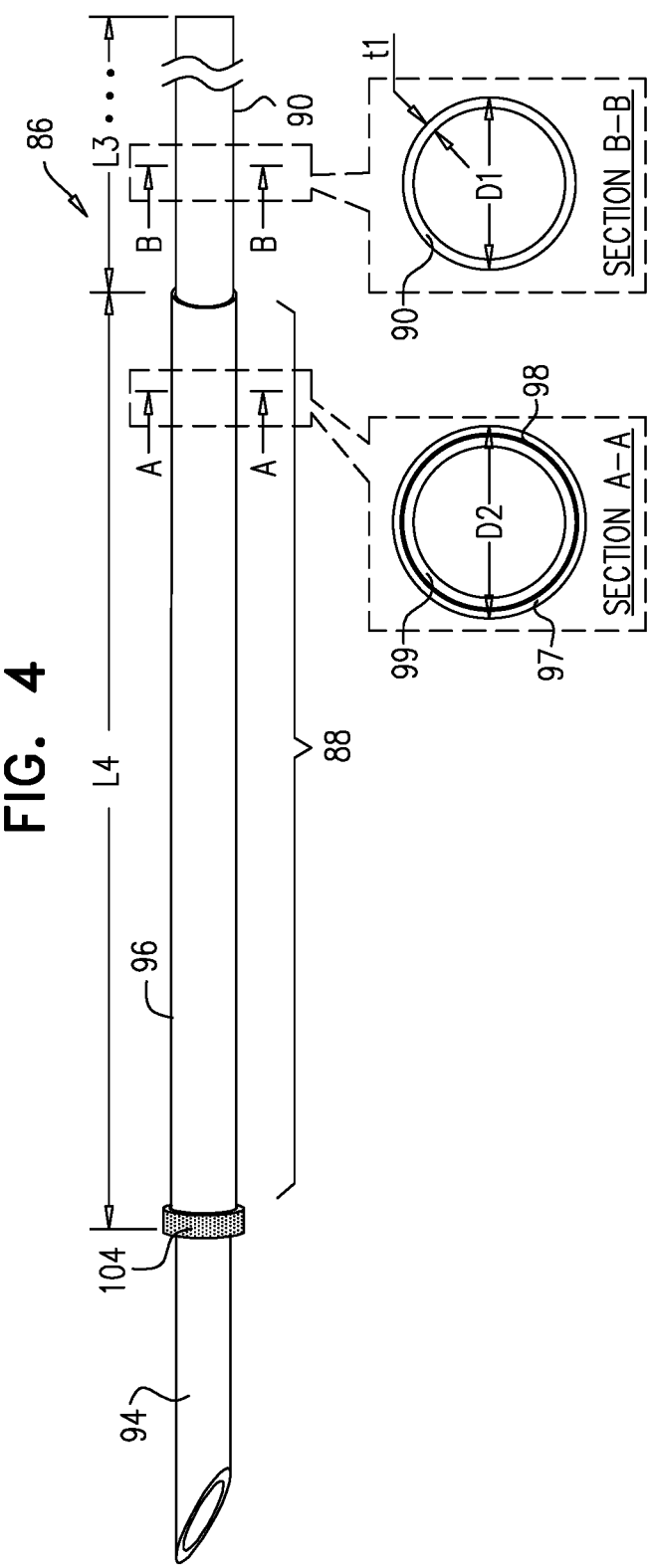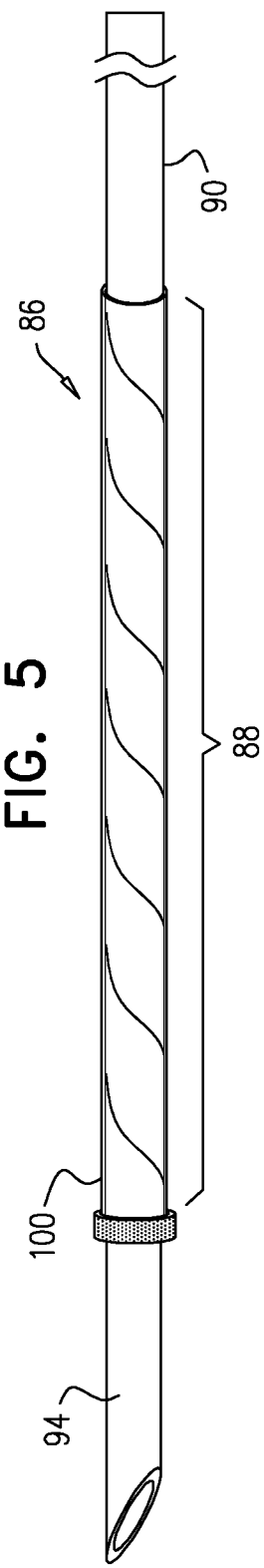

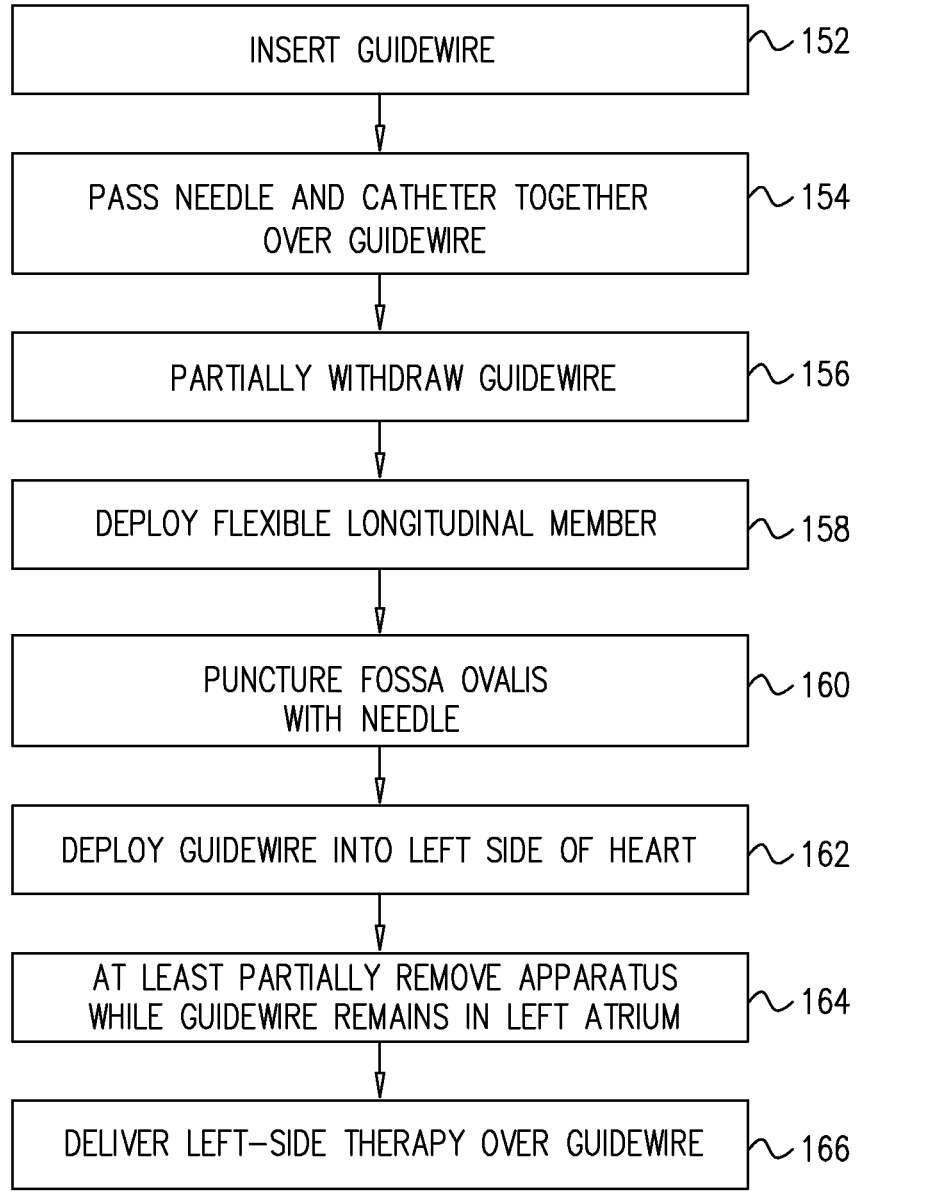

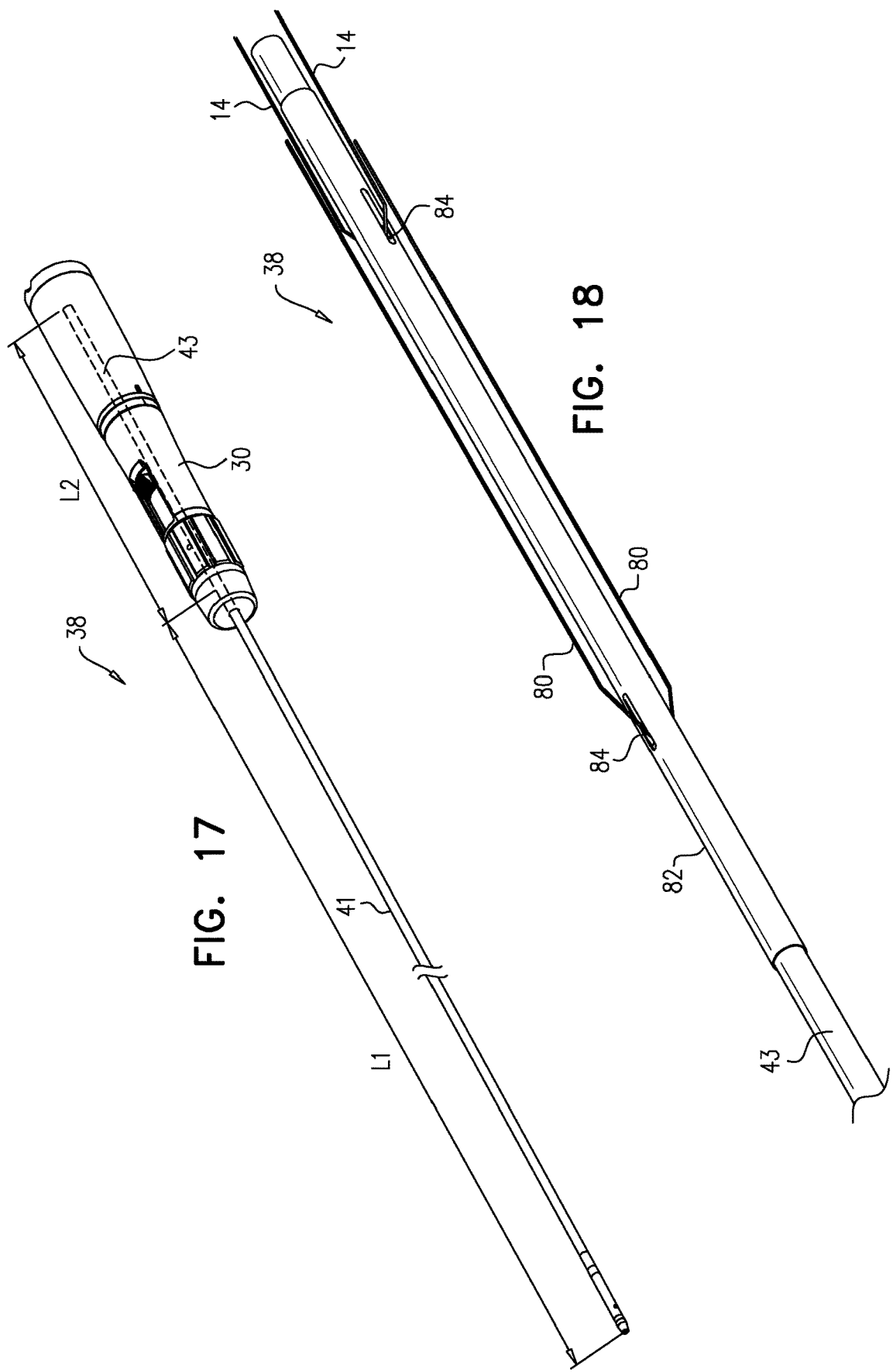

INTERATRIAL SEPTUM PENETRATION

CROSS-REFERENCE TO RELATED APPLICATIONS

The present application is a continuation of U.S. application Ser. No. 14/882,687, filed Oct. 14, 2015, now U.S. Pat. No. 10,398,503.

FIELD OF THE INVENTION

Applications of the present invention relate in general to the delivery of therapeutic devices to the left atrium or ventricle of the heart. More specifically, applications of the present invention relate to (a) penetrating the fossa ovalis for the purpose of delivering therapeutic devices, and/or (b) delivering an implant to the left atrial appendage.

BACKGROUND

Various pathologies call for the delivery of therapeutic devices, e.g., valve repair or valve replacement devices, to the left atrium or left ventricle of the heart (i.e., the left side of the heart). In many applications, therapeutic devices are delivered to the left side of the heart by being passed through the vena cava, into the right atrium, and through the interatrial septum. Such delivery calls for apparatus and methods for puncturing the interatrial septum. In many applications, the desired site for puncture lies in the fossa ovalis, a region of the septum containing tissue of lesser thickness than is typical of the rest of the septum.

SUMMARY OF THE INVENTION

Applications of the present invention include apparatus for forming a hole through an interatrial septum, such as at a fossa ovalis. The apparatus includes a catheter shaped to define a catheter lumen. The wall of the catheter includes a braided portion, and is shaped to define first and second longitudinally-running channels therethrough. A distal portion of the catheter is shaped to define first and second lateral openings, which are typically approximately equidistant from the distal end of the catheter. A wire passes through the first channel, out of the first channel via the first lateral opening, into the second channel via the second lateral opening, and through the second channel. The wire is deployed, i.e., pushed out of the catheter, such that the deployed portion of the wire is loop-shaped. The wire facilitates finding the fossa ovalis, and/or stabilizing the catheter as the fossa ovalis is punctured.

Applications of the present invention also include a catheter that has a wall having both a braided portion and an unbraided portion. A reinforcing tube at least partially surrounds the unbraided portion of the catheter wall. A control handle surrounds the catheter such that (a) all of the catheter wall that is distal to a distal end of the control handle comprises the braided portion, and (b) at least 10% of the catheter wall that is proximal to the distal end of the control handle comprises the unbraided portion.

Applications of the present invention also include various types of hollow needles having flexible distal portions.

Applications of the present invention also include a method that includes transvascularly inserting a guidewire into a right atrium of a subject. Apparatus is provided that includes (a) a catheter and (b) a hollow needle disposed within a lumen of the catheter, the hollow needle including a proximal portion and a distal portion that is more flexible than the proximal portion. The apparatus is passed into the right atrium by passing the needle over the guidewire. Following the passing of the apparatus into the right atrium, the guidewire is partially withdrawn into the needle, while keeping a distal end of the guidewire within the needle and in a body of the subject. Thereafter, a hole is formed through an interatrial septum (e.g., at a fossa ovalis) with the needle. Typically, after the hole is formed through the interatrial septum, the guidewire is advanced into a left atrium of the subject, and, thereafter, the needle is proximally withdrawn from the right atrium. Typically, after the needle is proximally withdrawn from the right atrium, a left-side therapeutic delivery system is introduced, over the guidewire, into the left atrium.

In general, apparatus and methods described herein can also be used to penetrate other body orifices. (In this context, penetration of the body orifice might not include puncturing with a puncturing element, as is typically the case for the fossa ovalis.) For example, apparatus and methods described herein can be used to pass a catheter and/or a therapeutic device through the coronary sinus ostium and into the coronary sinus. Furthermore, apparatus and methods described herein can also be used to locate an opening, natural or manmade, in a portion of anatomy. For example, apparatus and methods described herein can be used to locate the coronary sinus ostium, a natural opening in the fossa ovalis, or a puncture in the fossa ovalis. In some applications, apparatus described herein may be further configured to deliver a plug (e.g., an Amplatzer™), or other such stopping device, to the opening.

There is therefore provided, in accordance with an application of the present invention, a method including:

transvascularly inserting a guidewire into a right atrium of a subject;

providing apparatus that includes (a) a catheter and (b) a hollow needle disposed within a lumen of the catheter, the hollow needle including a proximal portion and a distal portion that is more flexible than the proximal portion;

passing the apparatus into the right atrium by passing the needle over the guidewire;

following the passing of the apparatus into the right atrium, partially withdrawing the guidewire into the needle, while keeping a distal end of the guidewire within the needle and in a body of the subject; and thereafter, forming a hole through an interatrial septum of the subject with the needle.

For some applications, the method further includes, after forming the hole through the interatrial septum, advancing the guidewire into a left atrium of the subject.

For some applications, the method further includes, after advancing the guidewire into the left atrium, proximally withdrawing the needle from the right atrium.

For some applications, the method further includes, after proximally withdrawing the needle from the right atrium, introducing, over the guidewire, a left-side therapeutic delivery system into the left atrium.

For some applications, proximally withdrawing the needle from the right atrium includes leaving the catheter in the right atrium, and introducing the left-side therapeutic delivery system includes introducing the left-side therapeutic delivery system through the catheter.

For some applications:

the method further includes, before introducing the left-side therapeutic delivery system into the left atrium, advancing the catheter distally through the hole into the left atrium, and introducing the left-side therapeutic delivery system into the left atrium includes advancing the left-side therapeutic delivery system through the catheter into the left atrium.

For some applications, forming the hole through the interatrial septum includes forming the hole through a fossa ovalis of the subject.

For some applications, forming the hole through the interatrial septum includes puncturing the interatrial septum with a sharp distal tip of the needle.

For some applications, forming the hole through the interatrial septum includes applying energy to the interatrial septum with the needle.

For some applications, the method further includes, before forming the hole through the interatrial septum:

deploying at least one fossa-ovalis-finding loop from a wall of the catheter; and moving the fossa-ovalis-finding loop along the interatrial septum, until the fossa-ovalis-finding loop contacts a fossa ovalis of the subject.

For some applications, partially withdrawing the guidewire includes partially withdrawing the guidewire a distance of less than 50 cm.

For some applications, the apparatus further includes a fluid-impermeable cover surrounding the distal portion of the needle.

For some applications, the method further includes measuring, using a pressure sensor disposed in fluid communication with a proximal end of the needle, a pressure at a distal tip of the needle.

For some applications:

the apparatus further includes a dilator element, which is shaped to define a dilator lumen and to be slidably disposed within the lumen of the catheter, the needle is slidably disposed within the dilator lumen, and the method further includes dilating the hole using the dilator element.

For some applications, the method further includes, after dilating the hole, advancing the catheter distally through the dilated hole into a left atrium of the subject.

For some applications, the hollow needle further includes a distal-most end portion that is less flexible than the flexible distal portion.

For some applications, the catheter is a puncture-tool catheter, and wherein passing the apparatus into the right atrium includes:

inserting a delivery catheter of a left-side therapeutic delivery system into the right atrium; and advancing the puncture-tool catheter through the delivery catheter into the right atrium.

For some applications, the distal portion of the hollow needle is helical.

There is still further provided, in accordance with an application of the present invention, a method including:

inserting a catheter into a right atrium of a heart of the subject;

advancing a distal portion of the catheter toward a fossa ovalis of the heart;

deploying a flexible longitudinal member from the catheter, such that a deployed portion of the flexible longitudinal member is loop-shaped;

contacting the fossa ovalis with the deployed portion of the flexible longitudinal member;

deploying a needle from the catheter;

bringing a distal end of the needle in contact with a site on a surface of an interatrial septum of the heart outside the fossa ovalis;

forming a hole through the interatrial septum at the site with the needle; and withdrawing the deployed portion of the flexible longitudinal member toward the catheter.

For some applications, forming the hole through the interatrial septum includes puncturing the interatrial septum with a sharp distal tip of the needle.

For some applications, forming the hole through the interatrial septum includes applying energy to the interatrial septum with the needle.

For some applications, contacting the fossa ovalis with the deployed portion of the flexible longitudinal member includes contacting an inner perimeter of the fossa ovalis.

For some applications, the method further includes, before contacting the fossa ovalis with the deployed portion of the flexible longitudinal member, moving the deployed portion of the flexible longitudinal member along the surface of the interatrial septum, until the flexible longitudinal member contacts the fossa ovalis.

For some applications, moving the deployed portion of the flexible longitudinal member along the surface of the interatrial septum includes moving the deployed portion of the flexible longitudinal member toward the fossa ovalis from below the fossa ovalis.

For some applications, deploying the flexible longitudinal member includes deploying the flexible longitudinal member such that a deployment angle of the flexible longitudinal member is between 10 and 80 degrees, the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point.

For some applications, deploying the flexible longitudinal member includes deploying the flexible longitudinal member such that the deployment angle is between 30 and 60 degrees.

For some applications, deploying the flexible longitudinal member from the catheter includes passing the flexible longitudinal member through two lateral openings at a distal portion of the catheter.

For some applications, the flexible longitudinal member is radiopaque, and the method further includes using fluoroscopic imaging to view the flexible longitudinal member during and after deployment thereof.

For some applications, the method further includes, before forming the hole through the interatrial septum, flexing a distal portion of the needle by steering the catheter.

For some applications, the catheter is a puncture-tool catheter, and inserting the catheter into the right atrium includes:

inserting a delivery catheter of a left-side therapeutic delivery system into the right atrium; and advancing the puncture-tool catheter through the delivery catheter into the right atrium.

There is additionally provided, in accordance with an application of the present invention, a method including:

inserting a catheter into a right atrium of a heart of a subject;

advancing a distal portion of the catheter toward a roof of the right atrium;

deploying a flexible longitudinal member from the catheter, such that a deployed portion of the flexible longitudinal member is loop-shaped;

contacting, with the deployed portion of the flexible longitudinal member, a stabilization site located (a) on the roof of the right atrium, (b) between the roof and an interatrial septum of the heart, or (c) on the interatrial septum superior to a fossa ovalis of the heart;

deploying a needle from the catheter;

bringing a distal end of the needle in contact with a hole site on a surface of the interatrial septum;

forming a hole through the interatrial septum at the hole site with the needle; and withdrawing the deployed portion of the flexible longitudinal member toward the catheter.

For some applications, forming the hole through the interatrial septum includes puncturing the interatrial septum with a sharp distal tip of the needle.

For some applications, forming the hole through the interatrial septum includes applying energy to the interatrial septum with the needle.

For some applications, deploying the flexible longitudinal member from the catheter includes passing the flexible longitudinal member through two lateral openings at a distal portion of the catheter.

For some applications, the flexible longitudinal member is radiopaque, and the method further includes using fluoroscopic imaging to view the flexible longitudinal member during and after deployment thereof.

For some applications, the method further includes, before forming the hole through the interatrial septum, flexing a distal portion of the needle by steering the catheter.

For some applications, the catheter is a puncture-tool catheter, and inserting the catheter into the right atrium includes:

inserting a delivery catheter of a left-side therapeutic delivery system into the right atrium; and advancing the puncture-tool catheter through the delivery catheter into the right atrium.

There is further provided, in accordance with some applications of the present invention, apparatus including:

a catheter shaped to define a catheter lumen, a wall of which catheter (a) comprising a braided portion having an outer surface, an inner surface, and a braided interior between the outer and inner surfaces, and (b) being shaped to define a first longitudinally-running channel therethrough and a second longitudinally-running channel therethrough, and a distal portion of which catheter being shaped to define a first lateral opening and a second lateral opening, an angle between (a) a first line running between the first and second lateral openings, and (b) a second line that is parallel to a central longitudinal axis of the catheter when the catheter is straight, being between 30 and 150 degrees; and a flexible longitudinal member that passes (a) from a proximal portion of the catheter to the distal portion of the catheter via the first channel, (b) out of the first channel via the first lateral opening, (b) into the second channel via the second lateral opening, and (c) from the distal portion of the catheter to the proximal portion of the catheter via the second channel.

In some applications, the angle between the first and second lines is between 60 and 120 degrees.

In some applications, the angle between the first and second lines is between 80 and 100 degrees.

In some applications, the first and second openings are separated from one another by an angle of 170-190 degrees measured along a circumference of the catheter.

In some applications, the apparatus further includes a needle shaped to be slidably disposed within the catheter lumen.

In some applications, the needle is electrically conductive, and the apparatus further comprises:

one or more conductors; and a controller, which is coupled to the needle by the conductors, and which is configured to drive the needle to apply energy capable of creating a hole through tissue.

In some applications, the apparatus further includes:

a dilator element shaped to be slidably disposed within the catheter lumen, the dilator element being shaped so as to define a dilator lumen; and a dilator tip disposed at a distal end of the dilator element, the dilator tip being configured to dilate an opening created by the needle.

In some applications, the needle is shaped to be slidably disposed within the dilator lumen.

In some applications, the flexible longitudinal member is mechanically resilient.

In some applications, a diameter of the flexible longitudinal member is between 0.1 and 0.5 mm.

In some applications, the flexible longitudinal member includes a wire.

In some applications, the flexible longitudinal member includes a material selected from the group consisting of: nitinol, stainless steel, and chromium cobalt.

In some applications, the flexible longitudinal member is configured to be deployed such that, in an absence of any force applied to the deployed portion of the flexible longitudinal member by an element that is not part of the apparatus, a deployment angle of the flexible longitudinal member is between 10 and 80 degrees, the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point.

In some applications, the flexible longitudinal member is configured to be deployed such that, in the absence of any force applied to the deployed portion of the flexible longitudinal member by an element that is not part of the apparatus, the deployment angle is between 30 and 60 degrees.

In some applications, the flexible longitudinal member is radiopaque.

In some applications, the apparatus further includes a plurality of radiopaque markers coupled to the flexible longitudinal member.

There is further provided, in accordance with some applications of the present invention, apparatus including:

a catheter having a catheter wall that comprises:

a braided portion having an outer surface, an inner surface, and a braided interior between the outer and inner surfaces; and an unbraided portion having an unbraided interior;

a control element shaped to surround a proximal portion of the catheter such that (a) all of the catheter wall that is distal to a distal end of the control element comprises the braided portion, and (b) at least 10% of the catheter wall that is proximal to the distal end of the control element comprises the unbraided portion; and a reinforcing tube at least partially surrounding the unbraided portion.

In some applications, a wall of the reinforcing tube is shaped to define one or more lateral openings therethrough, the catheter wall is shaped to define one or more longitudinally-running channels therethrough, and the apparatus further comprises one or more flexible longitudinal members passing through the lateral openings and through the longitudinally-running channels.

In some applications, the flexible longitudinal members are coupled to the control element.

In some applications, a length of the braided portion is between 600 and 1000 mm.

In some applications, a length of the unbraided portion is between 250 and 400 mm.

There is further provided, in accordance with some applications of the present invention, apparatus including:
a hollow needle comprising:
a proximal portion having an outer diameter between 0.7 and 3 mm, a length between 650 and 1200 mm, and a wall thickness between 0.1 and 0.3 mm; and
a helical distal portion having an outer diameter between 0.5 and 1.5 mm and a length between 50 and 200 mm; and
a fluid-impermeable cover surrounding the helical distal portion of the needle.

There is further provided, in accordance with some applications of the present invention, apparatus including:
a hollow needle comprising:
a proximal portion having an outer diameter between 0.7 and 3 mm, a length between 650 and 1200 mm, and a wall thickness between 0.1 and 0.3 mm; and
a laser-cut distal portion having an outer diameter between 0.5 and 1.5 mm and a length between 50 and 200 mm; and
a fluid-impermeable cover surrounding the laser-cut distal portion of the needle.

There is further provided, in accordance with some applications of the present invention, apparatus including:
a hollow needle comprising:
a proximal portion having an outer diameter between 0.7 and 3 mm, a length between 650 and 1200 mm, and a wall thickness between 0.1 and 0.3 mm; and
a distal portion (a) having an outer diameter between 0.5 and 1.5 mm and a length between 50 and 200 mm, and (b) comprising a wall that is shaped to define a plurality of openings that pass completely therethrough; and
a fluid-impermeable cover surrounding the laser-cut distal portion of the needle.

In some applications, the wall of the distal portion of the hollow needle is shaped to define a plurality of slits therethrough.

There is further provided, in accordance with some applications of the present invention, apparatus including:
a hollow needle comprising:
a proximal portion having an outer diameter between 0.7 and 3 mm, a length between 650 and 1200 mm, and a wall thickness between 0.1 and 0.3 mm; and
a distal portion comprising an elastomeric tube having an outer surface, an inner surface, and an interior portion between the outer and inner surfaces that is selected from the group consisting of: a braided metal interior, and a coiled metal interior,
the distal portion having an outer diameter between 0.5 and 1.5 mm and a length between 50 and 200 mm.

There is further provided, in accordance with some applications of the present invention, apparatus including:
a hollow needle comprising:
a proximal portion having an outer diameter between 0.7 and 3 mm, a length between 650 and 1200 mm, and a wall thickness between 0.1 and 0.3 mm; and
a distal portion at least partially made of nitinol, the distal portion having an outer diameter between 0.5 and 1.5 mm and a length between 50 and 200 mm.

There is further provided, in accordance with some applications of the present invention, a method for puncturing a fossa ovalis of a heart, the method including:
inserting a catheter into a right atrium of the heart;
advancing a distal portion of the catheter toward the fossa ovalis;
deploying a flexible longitudinal member and a needle from the catheter, such that (a) a deployed portion of the flexible longitudinal member is loop-shaped, and (b) the needle is on a first side of the deployed portion of the flexible longitudinal member;
contacting the fossa ovalis with the deployed portion of the flexible longitudinal member;
passing a distal end of the needle through the deployed portion of the flexible longitudinal member to a second side of the deployed portion of the flexible longitudinal member that is opposite the first side, and puncturing the fossa ovalis with the needle; and
while the distal end of the needle is on the second side of the deployed portion of the flexible longitudinal member, withdrawing the deployed portion of the flexible longitudinal member toward the catheter.

In some applications, contacting the fossa ovalis with the deployed portion of the flexible longitudinal member includes contacting an inner perimeter of the fossa ovalis.

In some applications, the method further includes, before contacting the fossa ovalis with the deployed portion of the flexible longitudinal member, moving the deployed portion of the flexible longitudinal member along a surface of an interatrial septum of the heart, until the flexible longitudinal member contacts the fossa ovalis.

In some applications, moving the deployed portion of the flexible longitudinal member along the surface of the interatrial septum includes moving the deployed portion of the flexible longitudinal member toward the fossa ovalis from below the fossa ovalis.

In some applications, deploying the flexible longitudinal member includes deploying the flexible longitudinal member such that a deployment angle of the flexible longitudinal member is between 10 and 80 degrees,
the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point.

In some applications, deploying the flexible longitudinal member includes deploying the flexible longitudinal member such that the deployment angle is between 30 and 60 degrees.

In some applications, deploying the flexible longitudinal member from the catheter includes passing the flexible longitudinal member through two lateral openings at a distal portion of the catheter.

In some applications, the flexible longitudinal member is radiopaque, and the method further includes using fluoroscopic imaging to view the flexible longitudinal member during and after deployment thereof.

In some applications, the method further includes, before puncturing the fossa ovalis, flexing a distal portion of the needle by steering the catheter.

In some applications, the catheter is a puncture-tool catheter, and inserting the puncture-tool catheter into the right atrium includes:

inserting a delivery catheter of a left-side therapeutic delivery system into the right atrium; and advancing the puncture-tool catheter through the delivery catheter into the right atrium.

There is further provided, in accordance with some applications of the present invention, a method for puncturing a fossa ovalis of a heart, the method including:

inserting a catheter into a right atrium of the heart;

advancing the catheter toward an interatrial septum of the heart;

subsequently, inserting a needle into a lumen of the catheter;

flexing a distal portion of the needle by steering the catheter; and following the flexing of the distal portion of the needle, using the needle to puncture the fossa ovalis.

There is further provided, in accordance with some applications of the present invention, apparatus including:

a hollow needle including:
a proximal portion; and
a helical distal portion; and
a fluid-impermeable cover surrounding the helical distal portion of the needle.

In some applications, the fluid-impermeable cover fits snugly around the helical distal portion of the needle.

In some applications, the proximal portion has an outer diameter between 0.7 and 3 mm.

In some applications, the proximal portion has a length between 650 and 1200 mm.

In some applications, the proximal portion has a wall thickness between 0.1 and 0.3 mm.

In some applications, the distal portion has an outer diameter between 0.5 and 1.5 mm.

In some applications, the distal portion has a length between 30 and 200 mm.

In some applications, the distal portion has a length between 30 and 100 mm.

In some applications, the helical distal portion includes a helically-cut tube.

In some applications, the helical distal portion includes one or more coiled wires.

There is further provided, in accordance with some applications of the present invention, apparatus including:

a hollow needle including:
a proximal portion; and
a distal portion that is more flexible than the proximal portion; and
a fluid-impermeable cover surrounding the distal portion of the needle.

In some applications, the distal portion includes a wall that is cut at one or more locations between longitudinal ends of the wall.

There is further provided, in accordance with some applications of the present invention, apparatus including:

a hollow needle including:
a proximal portion; and
a distal portion including a wall that is shaped to define a plurality of openings that pass completely therethrough; and
a fluid-impermeable cover surrounding the distal portion of the needle.

In some applications, the wall of the distal portion of the hollow needle is shaped to define 25-250 openings.

In some applications, the wall of the distal portion of the hollow needle is shaped to define a plurality of slits therethrough.

There is further provided, in accordance with some applications of the present invention, apparatus including:

a hollow needle including:
a proximal portion; and
a distal portion including an elastomeric tube having an outer surface, an inner surface, and an interior portion between the outer and inner surfaces that is selected from the group consisting of: a braided metal interior, and a coiled metal interior.

There is further provided, in accordance with some applications of the present invention, apparatus including:

a hollow needle including:
a proximal portion having an outer diameter between 0.7 and 3 mm, a length between 650 and 1200 mm, and a wall thickness between 0.1 and 0.3 mm; and
a distal portion at least partially made of nitinol, the distal portion having an outer diameter between 0.5 and 1.5 mm and a length between 30 and 200 mm.

There is further provided, in accordance with some applications of the present invention, apparatus including:

a tube shaped to define a tube lumen, a reduced-diameter portion of the tube lumen that is between 5 and 30 mm of a distal end of the tube having a diameter that is reduced, relative to a portion of the tube lumen that is proximal to the reduced-diameter portion; and a hollow needle, including:
a proximal portion;
a distal portion that is more flexible than the proximal portion; and
a distal-most end portion that is distal to the distal portion and is less flexible than the distal portion, the distal-most end portion including an increased-diameter portion having a diameter that is greater than another part of the distal-most end portion, the diameter of the reduced-diameter portion of the tube lumen being (a) less than an outer diameter of the increased-diameter portion, and (b) greater than an outer diameter of the other part of the distal-most end portion.

In some applications, the distal-most end portion has a length between 10 and 30 mm.

In some applications, the increased-diameter portion is disposed at a proximal end of the distal-most end portion.

In some applications, the outer diameter of the increased-diameter portion is greater than an outer diameter of the distal portion.

The present invention will be more fully understood from the following detailed description of applications thereof, taken together with the drawings, in which:

BRIEF DESCRIPTION OF THE DRAWINGS

FIGS. 1A-G are schematic illustrations of apparatus for puncturing a fossa ovalis of a subject, in accordance with some applications of the present invention;

FIGS. 4-7 are schematic illustrations of hollow needles having flexible distal portions, in accordance with some applications of the present invention;

FIG. 10 is a flow chart showing the steps in a method for puncturing a fossa ovalis with a hollow needle, in accordance with some applications of the present invention;

FIGS. 17-18 are schematic illustrations of a catheter, in accordance with some applications of the present invention.

DETAILED DESCRIPTION OF APPLICATIONS

Reference is now made to FIGS. 1A-G, which are schematic illustrations of apparatus 34 for puncturing a fossa ovalis 18 of a subject, and a method of using apparatus 34, in accordance with some applications of the present invention. Apparatus 34 comprises a catheter 38, which may also be referred to by those in the field as an introducer tube. Catheter 38 is shaped to define a catheter lumen 52.

Figure 1A:
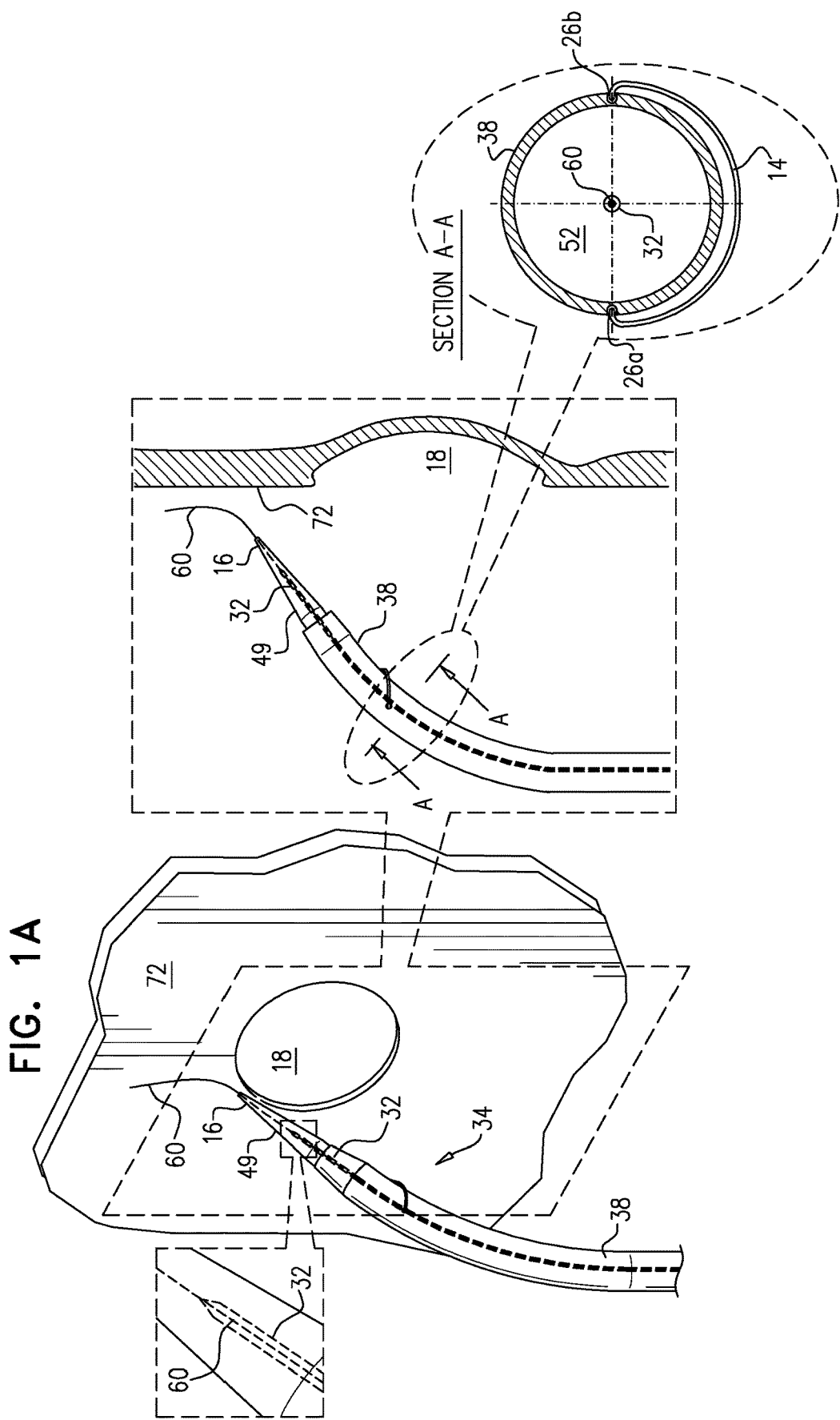
Figure 2A:
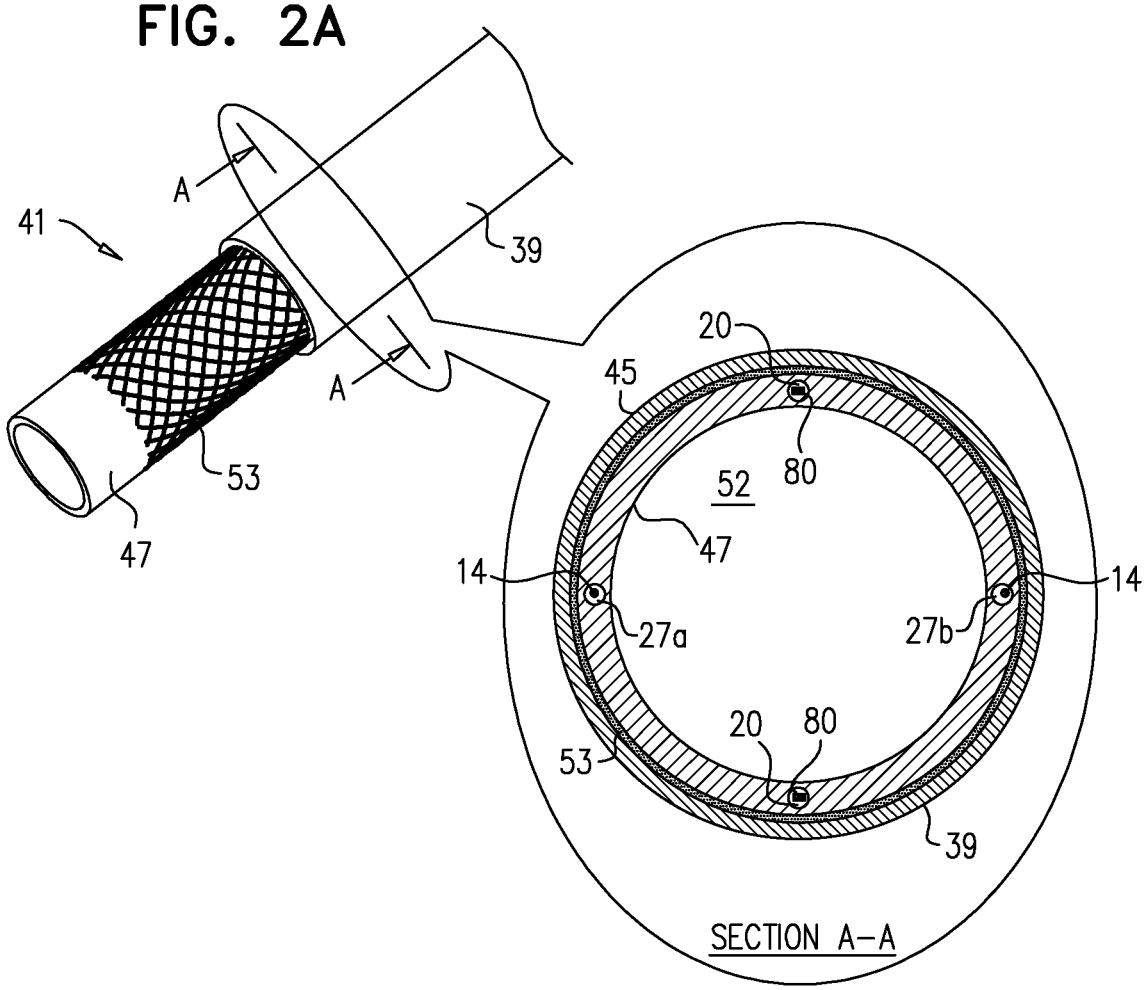
FIGS. 2A-B are schematic illustrations of a cross-section of a wall of a catheter, in accordance with some applications of the present invention.
Figure 2B:
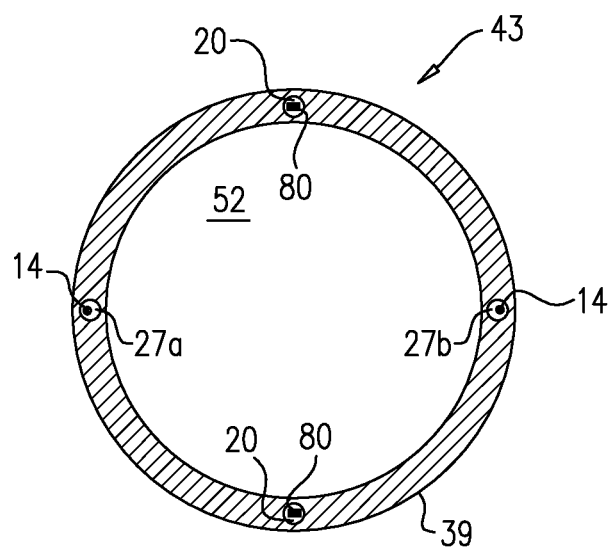

Reference is also made to FIGS. 2A-B, which are schematic illustrations of a cross-section of a wall 39 of catheter 38, in accordance with some applications of the present invention. Wall 39 comprises a braided portion 41 (shown in FIG. 2A), which has an outer surface 45, an inner surface 47, and a braided interior 53 between outer surface 45 and inner surface 47. Wall 39 also comprises an unbraided portion 43 (shown in cross-section in FIG. 2B), which is typically disposed proximally to braided portion 41. (Braided portion 41 and unbraided portion 43 are described in more detail hereinbelow with reference to FIGS. 17-18.) Wall 39 is shaped to define a first longitudinally-running channel 27a and a second longitudinally-running channel 27b therethrough. (Channels 27a and 27b run through both the braided and unbraided portions.) A distal portion of catheter 38 is shaped to define a first lateral opening 26a and a second lateral opening 26b (shown in FIG. 1A). A flexible longitudinal member 14 (e.g., a wire) passes (a) from a proximal portion of the catheter to the distal portion of the catheter via first channel 27a, (b) out of first channel 27a via first lateral opening 26a, (c) into second channel 27b via second lateral opening 26b, and (d) from the distal portion of the catheter to the proximal portion of the catheter via second channel 27b.

Typically, flexible longitudinal member 14 is mechanically resilient, i.e., it does not readily buckle upon being subjected to a compressive force, as would, for example, a string. The flexible longitudinal member typically comprises nitinol, stainless steel, and/or chromium cobalt, and typically has a diameter D that is at least 0.1 mm and/or less than 0.5 mm.

Figure 3:
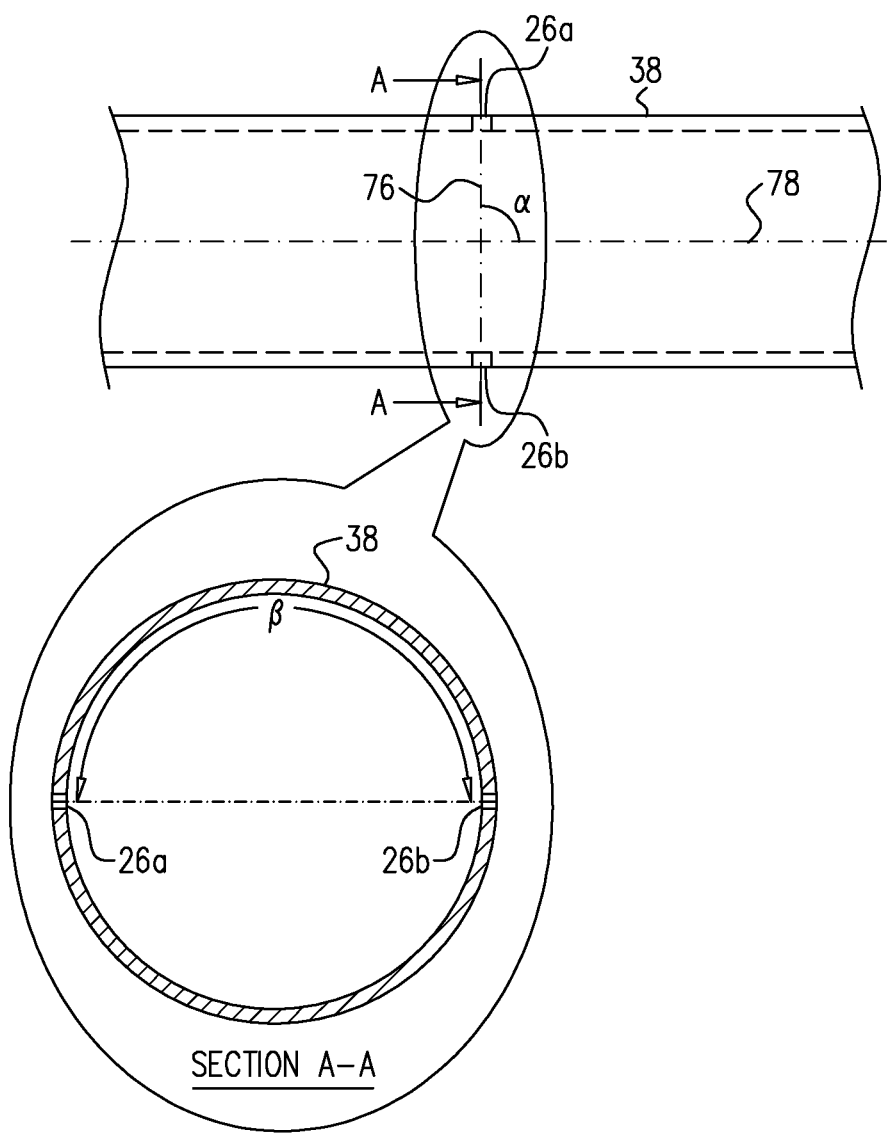
FIG. 3 is a schematic illustration of a catheter, in accordance with some applications of the present invention.

Reference is now made to FIG. 3, which is a schematic illustration of catheter 38, in accordance with some applications of the present invention. Typically, first and second openings 26a and 26b are disposed at substantially the same distance from the distal end of the catheter. An advantage of this disposition is that the loop may be deployed in a forward-facing direction, rather than laterally. For example, an angle alpha between (a) a first line 76 running between the first and second lateral openings, and (b) a second line 78 that is parallel to a central longitudinal axis of the catheter when the catheter is straight, may be at least 30 and/or less than 150 degrees, e.g., between 60 and 120 degrees, e.g., between 80 and 100 degrees. (An angle alpha of 90 degrees implies that the first and second openings are disposed at the same distance from the distal end of the catheter.) Alternatively or additionally, the distance of one opening from the distal end of the catheter differs by less than 1 cm from the distance of the other opening.

Further typically, the first and second openings are separated from one another by an angle beta of at least 170 degrees and/or less than 190 degrees (e.g., 180 degrees) measured along a circumference of the catheter. Thus, when the flexible longitudinal member is in its withdrawn position, it "occupies" only 170-190 degrees around the outside surface of the catheter, both prior to deployment and following withdrawal. In contrast, if beta were farther away from 180 degrees, the withdrawn flexible longitudinal member might occupy a relatively large angle, either prior to deployment or following withdrawal. For example, if beta were 90 degrees, the flexible longitudinal member would typically occupy 270 degrees either prior to deployment or following withdrawal, if, as described hereinbelow with reference to FIG. 1E, the deployment and withdrawal of the flexible longitudinal member are done from/toward opposite sides of the catheter. It is typically preferred that such a large portion of the flexible longitudinal member not be disposed outside of the catheter when the flexible longitudinal member is in its withdrawn position, since the risk of collateral damage to tissue typically increases as more of the flexible longitudinal member is exposed. The angle beta of 170-190 degrees is thus advantageous, particularly when the deployment and withdrawal are done from/to opposite sides of the catheter. (It is noted that for some procedures or for some patients, an angle beta outside of 170-190 degrees is appropriate.)

Reference is now made to FIGS. 4-7, which are schematic illustrations of a hollow needle 32 having a flexible distal portion 88, in accordance with some applications of the present invention. The applications shown in FIGS. 4-7 are similar to each other in function; they differ from each other mainly in the structure of flexible distal portion 88. An advantage of needle 32 is that flexible distal portion 88 of the needle is more flexible than other portions of the needle (e.g., than a proximal portion 90 of the needle), such that flexible distal portion 88, while inside the catheter lumen, may be flexed by steering the catheter. Another advantage of flexible distal portion 88 of needle 32 is that if the needle were instead stiff, rather than flexible, the needle might cut the guidewire as a sharp distal tip of the needle is forced against the outer surface of the guidewire during advancement of the needle over the guidewire.

Needle 32 comprises proximal portion 90, which generally runs through most of the length of the catheter, and which is used to transfer pushing force to the distal portion of the needle (and is therefore typically stiffer than flexible distal portion 88). Proximal portion 90 typically has an outer diameter D1 that is at least 0.7 mm and/or less than 3 mm, and/or a length L3 that is at least 650 mm and/or less than 1200 mm, and/or a wall thickness t1 that is at least 0.1 mm and/or less than 0.3 mm. Flexible distal portion 88 typically has an outer diameter D2 that is at least 0.5 mm and/or less than 1.5 mm, and/or a length L4 that is at least 30 mm and/or less than 200 mm, e.g., between 30 and 100 mm. Needle 32 also comprises a distal-most end portion 94, which is less flexible than flexible distal portion 88, and is typically relatively rigid. (The relative rigidity of distal-most end portion 94 facilitates the puncturing function of the needle.) In some applications, the distal-most end portion comprises an increased-diameter portion 104 having a diameter that is greater than the other part of the distal-most end portion. Increased-diameter portion 104 is typically disposed at the proximal end of the distal-most end portion. The function of the increased-diameter portion is described below with reference to FIG. 8.

In FIG. 4, flexible distal portion 88 of the needle comprises an elastomeric tube 96 having an outer surface 97, an inner surface 99, and a braided and/or coiled metal interior 98 between the inner and outer surfaces. (Thus flexible distal portion 88 may be structurally similar to the braided portion of the catheter, shown in FIG. 2A.) Elastomeric tube 96 provides flexibility to flexible distal portion 88. Braided and/or coiled metal interior 98 reinforces the elastomeric tube such that it is less susceptible to buckling, and also facilitates the transfer of electric current between the distal and proximal ends of the needle. The transfer of electric current may be used to verify that the needle has punctured the fossa ovalis, and/or apply an ablating current, e.g., a radiofrequency (RF) current, or other energy (e.g., heat, ultrasound, or light (e.g., laser) energy) to puncture the fossa ovalis.

Figure 6:
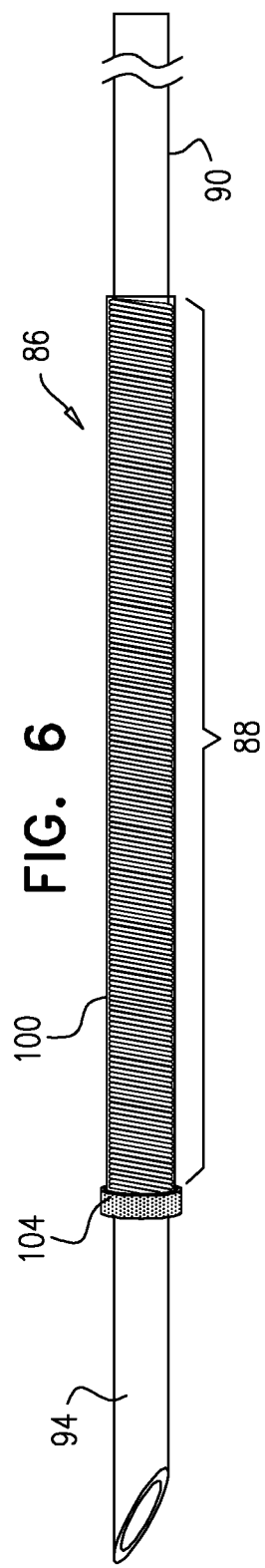

The applications of FIGS. 5-6 are similar to that of FIG. 4 in that (a) the dimensions of flexible distal portion 88 and proximal portion 90 are generally as described above, and (b) flexible distal portion 88 is more flexible than other portions of the needle. (The applications of FIGS. 5-6 also provide for the transfer of electric current via flexible distal portion 88.) The applications of FIGS. 5-6 differ from that of FIG. 4 in that the flexibility of the distal portion is facilitated by the helical configuration of the distal portion, rather than by elastomeric tube 96. The helical configuration of the distal portion may be achieved, for example, by cutting (e.g., laser-cutting) a tube (e.g., a metallic tube), as in FIG. 5, or by coiling one or more wires (e.g., metallic wires), as in FIG. 6.

Figure 7:
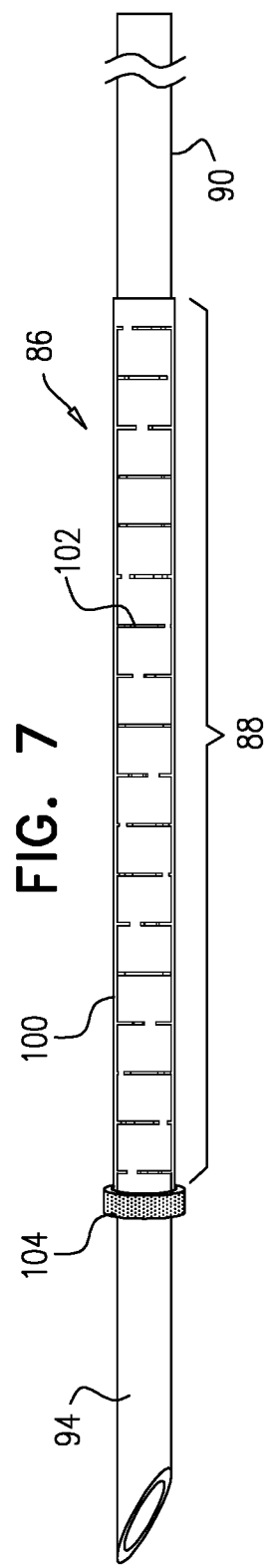

The application of FIG. 7 is similar to those of FIGS. 5-6 in that (a) the dimensions of flexible distal portion 88 and proximal portion 90 are generally as described above, and (b) flexible distal portion 88 is more flexible than other portions of the needle. Furthermore, the application of FIG. 7 is similar to that of FIG. 5 in that the respective configurations of the distal portions may be achieved via cutting (e.g., laser-cutting) a tube wall at one or more locations between longitudinal ends of the wall. (The application of FIG. 7 also provides for the transfer of electric current via flexible distal portion 88.) The application of FIG. 7 differs from those of FIGS. 5-6 in that the flexibility of flexible distal portion 88 is facilitated by the wall of the flexible distal portion being shaped to define a plurality of openings 102 (e.g., slits) that pass completely therethrough. Typically, the number of openings 102 is at least 25 and/or less than 250.

For the applications of FIGS. 5-7, in order to keep the lumen of the needle fluidly isolated from the needle's environment, a fluid-impermeable cover 100 (e.g., a polymer film) surrounds (e.g., fits snugly around) the distal portion of the needle. (Also typically, the distal portion is internally lined by a lining such as a polymer film.) By keeping the lumen of the needle fluidly isolated, fluid-impermeable cover 100 facilitates measurement, using a pressure sensor disposed in fluid communication with the proximal end of the needle, of the pressure at the distal tip of the needle. (Elastomeric tube 96, shown in FIG. 4, is also fluid-impermeable, and also facilitates pressure measurements.)

In general, flexible distal portion 88 may include various combinations or subcombinations of elements from FIGS. 4-7. Furthermore, in some applications, flexible distal portion 88 comprises a portion that is at least partially made of nitinol; for example, braided and/or coiled metal interior 98 (FIG. 4) may be at least partially made of nitinol. The nitinol provides flexibility to flexible distal portion 88, while also facilitating the transfer of electric current. Similarly, distal-most end portion 94 and/or proximal portion 90 may be at least partially made of nitinol. Typically, portions of the flexible needles of FIGS. 4-7 include stainless steel and/or another metal such as titanium, alternatively or additionally to nitinol.

Figure 8:
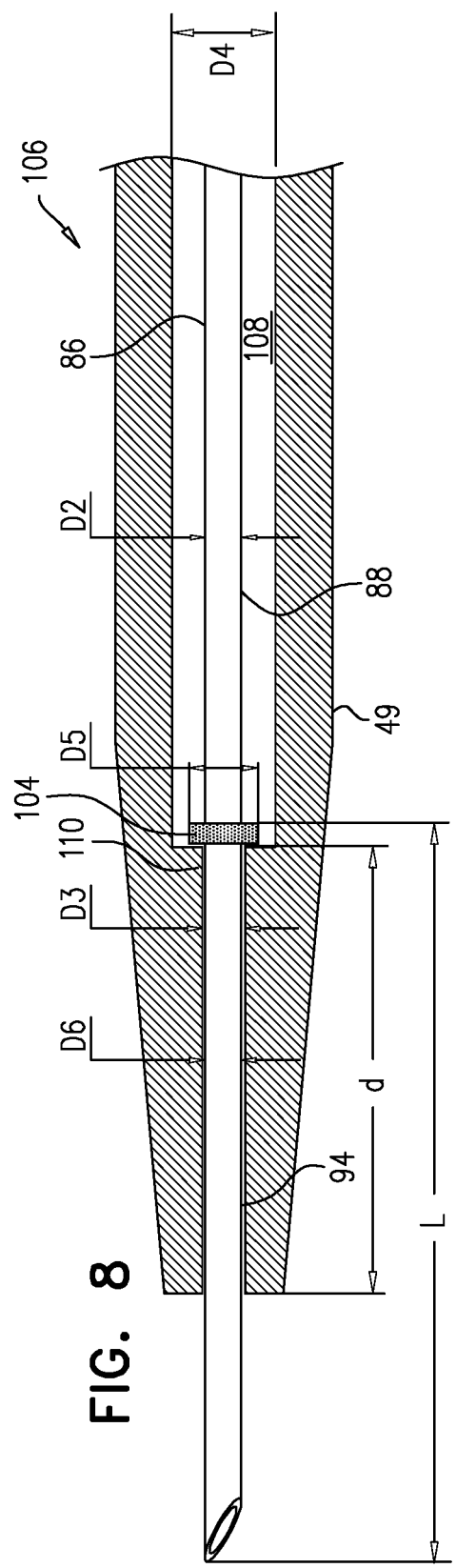
FIG. 8 is a schematic illustration of apparatus used, for example, for fossa ovalis penetration, in accordance with some applications of the present invention.

Reference is now made to FIG. 8, which is a schematic illustration of apparatus 106 used, for example, for fossa ovalis penetration, in accordance with some applications of the present invention. Apparatus 106 includes a tube, such as a dilator element 49, shaped to define a tube lumen 108. A reduced-diameter portion 110 of the tube lumen is located at a distance d from the distal end of the tube, d being at least 5 mm and/or less than 30 mm. Reduced-diameter portion 110, which may include a protrusion and/or a narrowing of the tube lumen, has a diameter D3 that is reduced, relative to a portion of the tube lumen that is proximal to the reduced-diameter portion. For example, in FIG. 8, the portion of the tube lumen that is proximal to the reduced-diameter portion has a diameter D4 that is greater than D3.

Apparatus 106 also includes hollow needle 32, described hereinabove with reference to FIGS. 4-7. Diameter D3 of the reduced-diameter portion of the tube lumen is less than the outer diameter D5 of increased-diameter portion 104 of the distal-most end portion of the needle, but is greater than the outer diameter D6 of the other part of the distal-most end portion. Hence, only the part of the distal-most end portion that is distal to the increased-diameter portion advances past the reduced-diameter portion of the tube lumen. (Typically, diameter D5 is also greater than outer diameter D2 of flexible distal portion 88.)

In some applications, distal-most end portion 94 has a length L that is at least 10 mm and/or less than 30 mm. In some applications, the increased-diameter portion is formed by attaching a ring to part of the distal-most end portion of the needle. The ring is attached at a distance from the distal tip of the needle that corresponds to the desired amount of protrusion of the needle. (Typically, the ring is permanently attached.) In other applications, the distal-most end portion of the needle is shaped during manufacture to define the increased-diameter portion.

Reference is made to FIGS. 4-8. It is noted that the use of hollow needle 32 may be particularly advantageous when flexible longitudinal member 14 (or other fossa-ovalis-locating-facilitating apparatus, such as those described in US 2014/0309675 to Maisano, which is incorporated herein by reference) is deployed from the catheter. Flexible longitudinal member 14 provides a "buffer" between the catheter and septum (see FIG. 1C), allowing the catheter to be steered without significant risk of accidentally puncturing the septum. In other words, without flexible longitudinal member 14, it might not be practical to steer the catheter, even if the needle were to have a flexible distal portion. Thus there is a particular synergy that is obtained when flexible longitudinal member 14 is used together with hollow needle 32.

Figure 9:
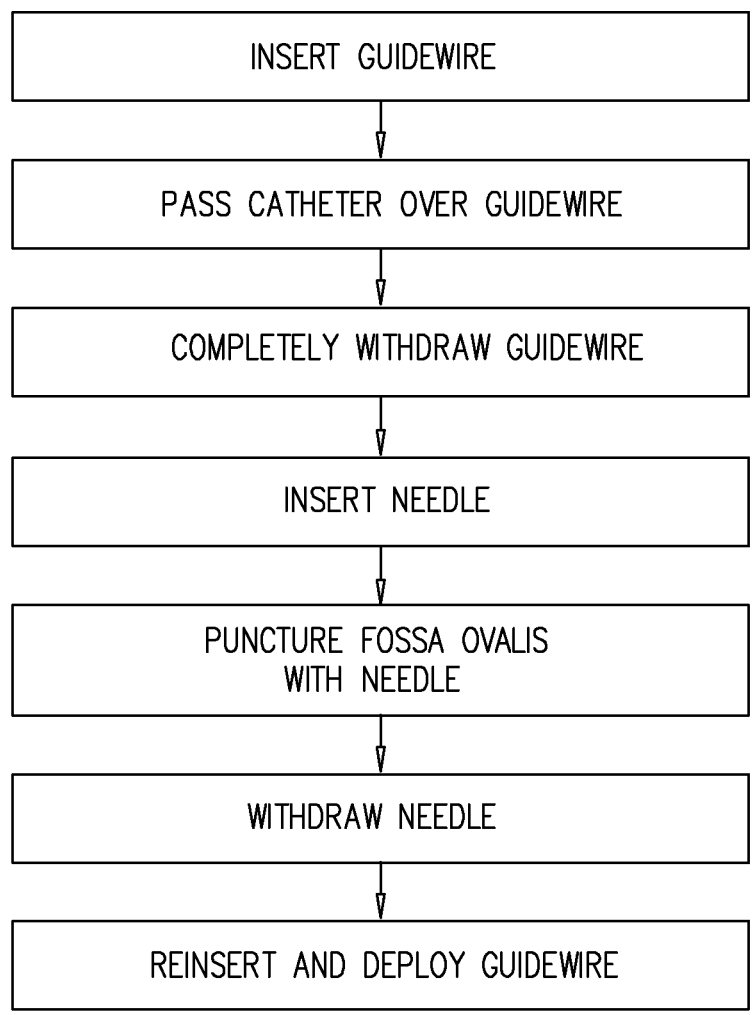
FIG. 9 is a flow chart showing the steps in a prior-art method for puncturing a fossa ovalis and delivering treatment to a left side of a heart.

Reference is now made to FIG. 9, which is a flow chart showing a prior-art method for puncturing a fossa ovalis and delivering treatment to a left side of a heart. Part of the prior-art method depicted in FIG. 9 is described in (i) an Instructions for Use (IFU) document for the BRK™ Transseptal Needle, dated Mar. 25, 2010, released by St. Jude Medical, and (ii) an IFU document for the Swartz™ Braided Transseptal Guiding Introducer, dated Feb. 4, 2010, also released by St. Jude Medical.

In the prior-art method, the needle is pre-shaped, and thus cannot be passed over a guidewire, lest the needle tear through or otherwise distort the guidewire. (Such tearing and/or distortion would inhibit performance of the procedure, and, furthermore, would typically result in the needle damaging the dilator and/or catheter.) Therefore, after passing the catheter over the guidewire, the guidewire is completely withdrawn from the lumen of the catheter before the needle is inserted. Following the puncturing of the fossa ovalis and the passing of the catheter to the left side of the heart, the needle is withdrawn from the lumen of the catheter. The guidewire is then reinserted into the catheter and deployed into the left side of the heart, in order to facilitate the subsequent delivery of treatment to the left side of the heart.

In contrast with the prior art, an advantage of hollow needle 32 is that the needle typically does not require pre-shaping before being loaded into catheter 38, since, as noted above, the flexibility of flexible distal portion 88 of hollow needle 32 generally allows the needle to be flexed into its desired orientation while it is inside the catheter. Hence, the guidewire need not necessarily be withdrawn before insertion of the needle, since hollow needle 32 may be passed over the guidewire. Furthermore, following the passing of the catheter to the left side of the heart, the needle need not necessarily be withdrawn from the catheter to facilitate the deployment of the guidewire into the left side of the heart, since the guidewire may be deployed through the lumen of the needle. Thus the flexibility of the distal portion of hollow needle 32 may help shorten the time required to perform the procedure and simply the procedure.

Reference is now made to FIG. 10, which is a flow chart showing the steps of a method 151 for puncturing a fossa ovalis with hollow needle 32, in accordance with some applications of the present invention. Reference is also made again to FIGS. 1A-G. This method utilizes some of the above-noted advantages of hollow needle 32. In method 151, apparatus that includes at least catheter 38 and hollow needle 32 is provided. Typically, the provided apparatus further includes other elements, such as dilator element 49 and flexible longitudinal member 14.

At a guidewire-insertion step 152, a guidewire 60 is transvascularly inserted into the right atrium of the subject, typically by inserting the guidewire into a vein in the pelvic area of the subject (e.g., the femoral vein), and advancing the guidewire toward the heart through the inferior vena cava.

At an apparatus-passing step 154, apparatus 34 is passed into the right atrium by passing needle 32 (together with catheter 38, inside which the needle is disposed) over guidewire 60, as shown in FIG. 1A. (As noted above, there is typically no need to withdraw the guidewire before passing the needle into the right atrium.) Typically, dilator element 49, which is shaped to define a dilator lumen, is shaped to be slidably disposed within the catheter lumen, and the needle is shaped to be slidably disposed within the dilator lumen. The needle is inserted into the dilator lumen, and is advanced up to a tip 16 of the dilator element. (Although dilator element 49 may also be embodied as a catheter, the present description refers exclusively to catheter 38—the "introducer tube"—as a catheter.) (Typically, catheter 38 is contained within the lumen of a sheath during parts of the insertion and/or withdrawal of the catheter, such as to reduce the risk of damage to surrounding tissue.) Following the insertion into the right atrium, the distal portion of catheter 38 is advanced toward an interatrial septum 72 of the heart (FIG. 1A).

Figure 1B:
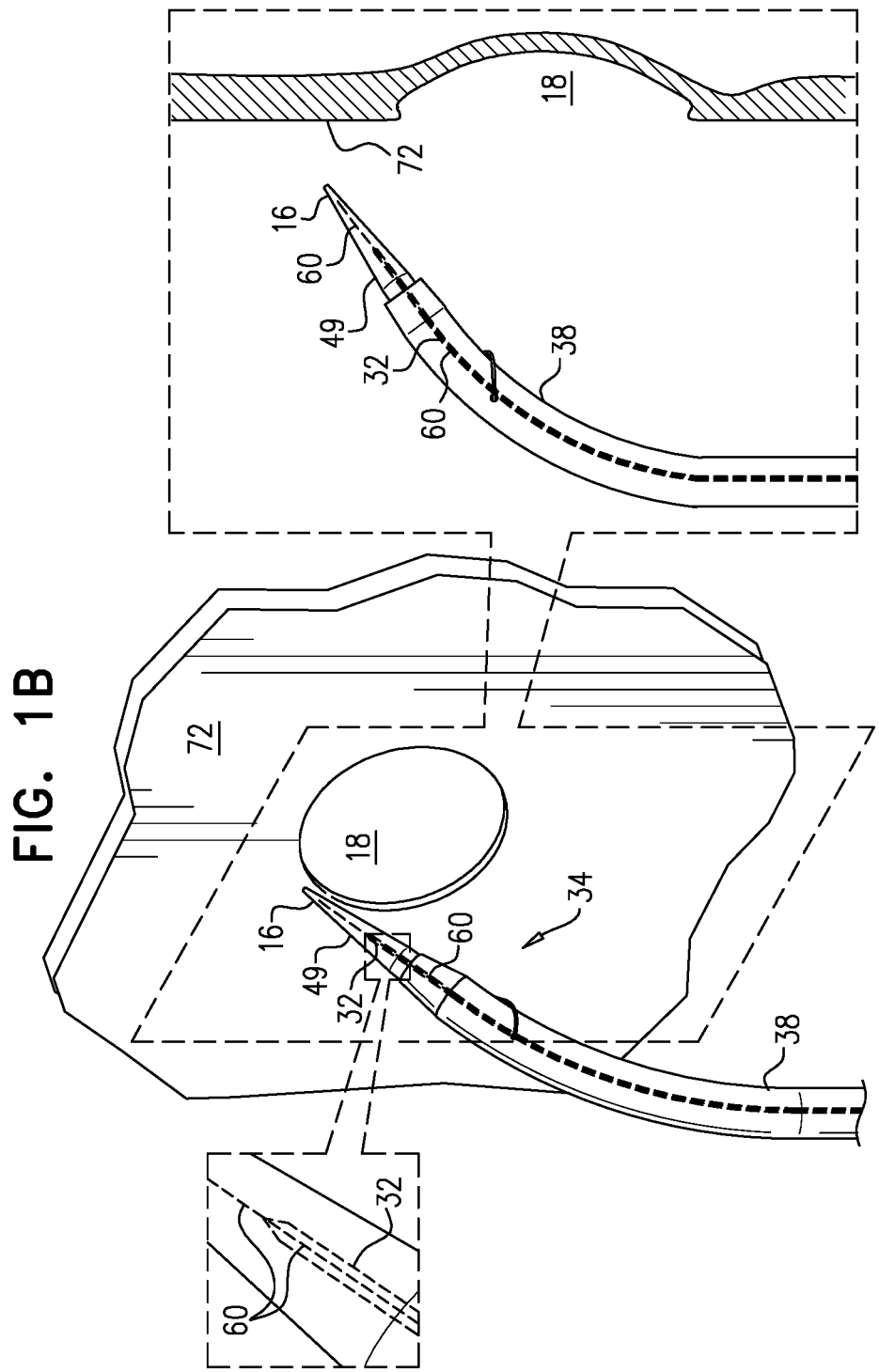

Following the passing of the apparatus into the right atrium, guidewire 60 is partially withdrawn until the distal end of the guidewire does not protrude from the distal end of needle 32, at a guidewire-partial-withdrawal step 156, as shown in FIG. 1B. Such partial withdrawal of the guidewire may expedite the post-puncture deployment of the guidewire into the left side of the heart. Upon being partially withdrawn, the guidewire remains inside the lumen of needle 32 and within the subject's body during the puncturing of the fossa ovalis. For example, the guidewire may be withdrawn a distance into the needle of between 0 cm (i.e., just to the distal tip of the needle) and 50 cm (e.g., to the proximal end of the needle, such as between 0 cm and 25 cm. In other applications, the guidewire is completely withdrawn from the catheter at guidewire-partial-withdrawal step 156.

Figure 1C:
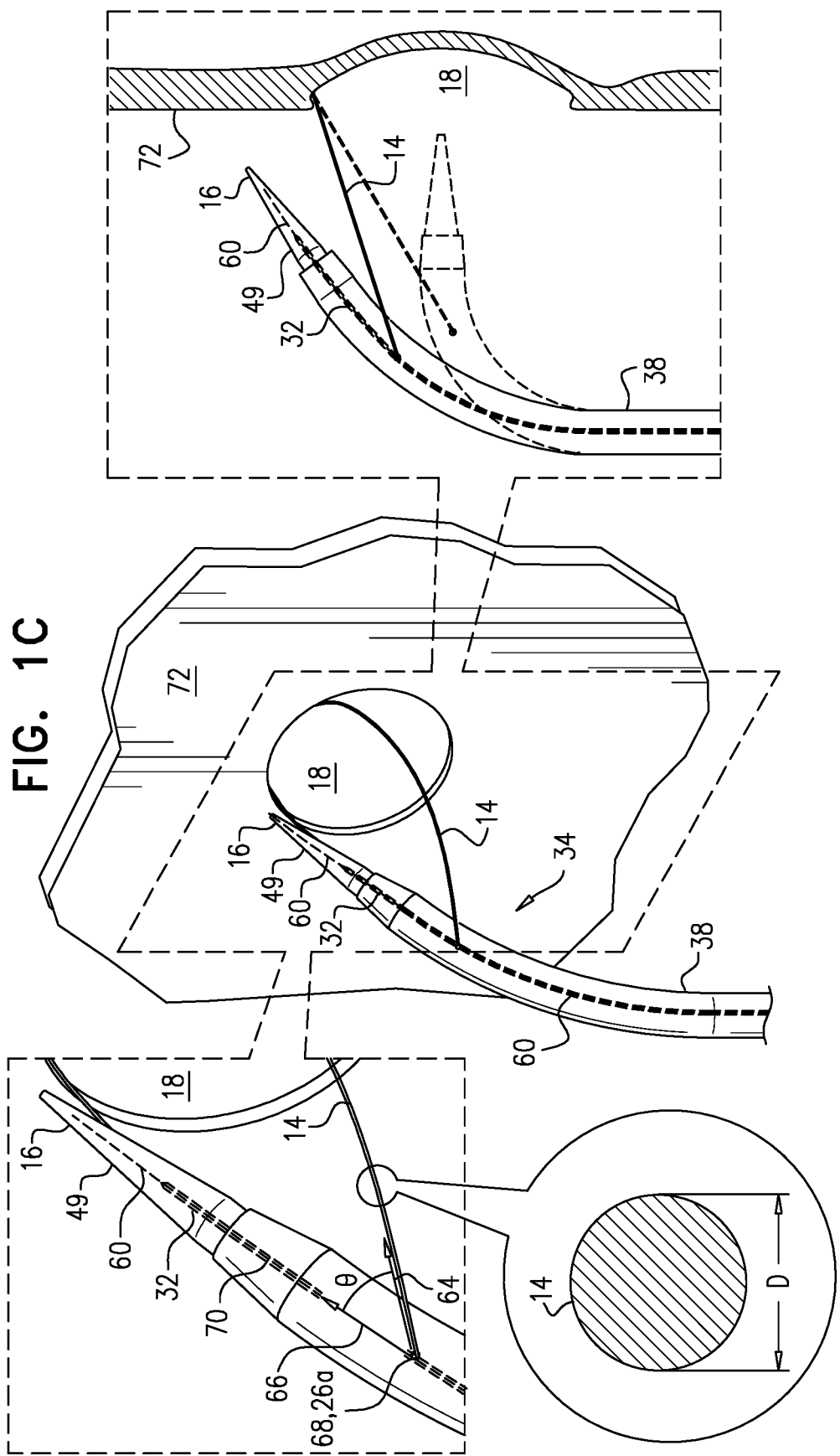

Typically, at a flexible-longitudinal-member-deployment step 158, as shown in FIG. 1C, flexible longitudinal member 14 (e.g., a fossa-ovalis-finding loop) is then deployed from the wall of the catheter, such that (i) a deployed portion of the flexible longitudinal member is loop-shaped, and (ii) the needle is on a first side of the deployed portion of the flexible longitudinal member. Typically, the flexible longitudinal member is deployed such that a deployment angle theta of the flexible longitudinal member is at least 10 degrees and/or less than 80 degrees, e.g., between 30 and 60 degrees. Deployment angle theta is defined as the angle between (a) a vector 64 that is tangent to the flexible longitudinal member at an exit point 68 of the flexible longitudinal member, and is directed away from the catheter, and (b) a distally-directed vector 66 that is parallel to the longitudinal axis 70 of the catheter at exit point 68. (Exit point 68 is identical to one of openings 26a and 26b.) As described hereinabove, the flexible longitudinal member is deployed by passing the flexible longitudinal member through openings 26a and 26b. The catheter is steered until fossa ovalis 18 (e.g., an inner perimeter of the fossa ovalis) is contacted with the deployed portion of the flexible longitudinal member, as shown in FIG. 1C. Alternatively, another site of the right atrial wall is contacted with the deployed portion of the flexible longitudinal member, as described hereinbelow with reference to FIG. 13.

Subsequently, at a fossa-ovalis-puncturing step 160, the fossa ovalis of the subject is punctured with the needle, as shown in FIG. 1D, typically while needle 32 is within dilator element 49, as shown in the figure. Typically, in order to puncture the fossa ovalis with the needle, dilator tip 16 is brought into contact with the fossa ovalis. The needle is then advanced through a distal opening of the dilator tip and through the fossa ovalis, thus puncturing a hole in the fossa ovalis. Dilator tip 16 then dilates the hole created by the needle, also as shown in FIG. 1D. Alternatively, interatrial septum 72 is punctured outside fossa ovalis 18, such as described hereinbelow with reference to FIG. 12. Further alternatively or additionally, the hole is created using energy applied with the needle, rather than force-based mechanical puncturing by the needle, as described hereinbelow with reference to FIG. 15.

As shown in FIG. 1D, prior to puncturing the fossa ovalis, the distal end of needle 32 is typically passed through the deployed portion of the flexible longitudinal member to a second side of the deployed portion of the flexible longitudinal member that is opposite the first side. (The distal end of the needle is typically passed through the loop while disposed inside of the dilator element.)

Typically, catheter 38 is flexibly and/or rotatably steerable via control wires 80 running through control-wire channels 20. The steerability of catheter 38 facilitates better localization of the desired puncturing point. Furthermore, a distal flexible portion of the needle (described hereinabove with reference to FIGS. 4-7), while it is inside the catheter lumen, may be flexed by steering the catheter. Following the flexing of the distal portion of the needle, the needle is used to puncture the fossa ovalis. The flexing of the needle facilitates the puncturing of the fossa ovalis at the desired location, and/or at the desired angle of the needle relative to the fossa ovalis. Furthermore, owing to the flexibility of the needle, there is generally no need to bend (i.e., pre-shape) the needle prior to insertion of the needle into the subject; rather, the needle may be advanced toward the heart of the subject while in a generally straight position, without necessarily using a stylet to maintain the straight position.

Figure 1E:
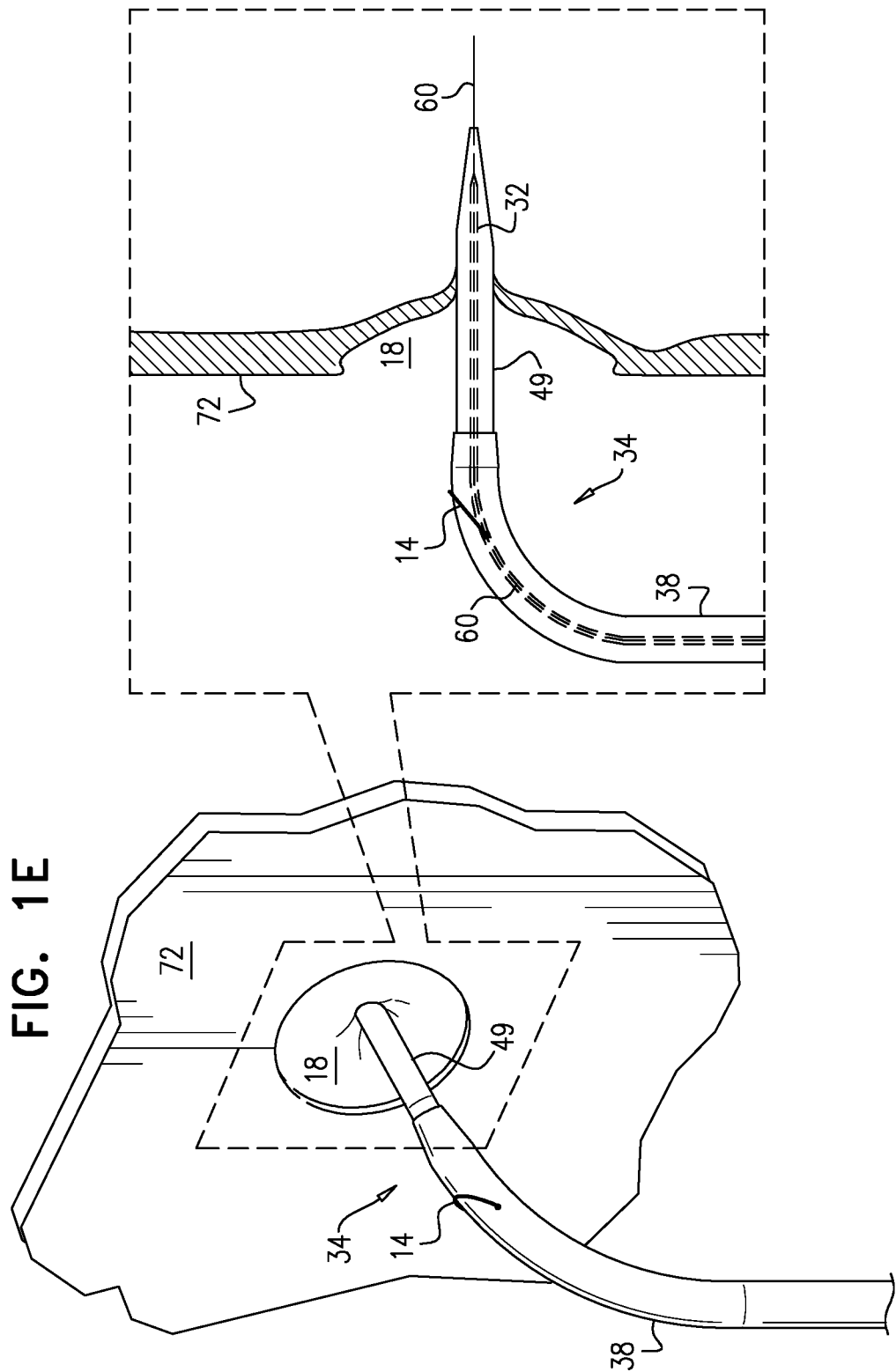

At a guidewire-deployment step 162, as shown in FIGS. 1D and 1E, guidewire 60 is deployed (i.e., advanced) into the left side of the heart (including into the left atrium), to facilitate the delivery of treatment. Guidewire 60 may be deployed into the left atrium along with needle 32 and/or dilator element 49, as shown in FIG. 1D, or guidewire 60 may be deployed into the left atrium after advancing needle 32 and/or dilator element 49 into the left atrium. Guidewire 60 is optionally advanced distally out of the distal end of the needle 32 and/or dilator element 49 while needle 32 and/or dilator element 49 are in the left atrium (as shown in FIG. 1E). Alternatively or additionally, needle 32 and/or dilator element 49 is withdrawn proximally while holding the guidewire axially stationary, such that the guidewire extends distally out of needle 32 and/or dilator element 49. In either case, such distal deployment of the guidewire may help avoid slippage of the guidewire into the right atrium as needle 32 and/or dilator element 49 is withdrawn into the left atrium, as described hereinbelow with reference to FIG. 1F. (As noted above, in some applications, the deployment of the guidewire is relatively quick, as the guidewire remains inside the lumen of the needle during the puncturing of the fossa ovalis.) For some applications, the deployed portion of flexible longitudinal member 14 is withdrawn toward the catheter while the distal end of the needle is on the second side of the deployed portion of the flexible longitudinal member (also as shown in FIG. 1E).

At an apparatus removal step 164, at least a portion (e.g., all) of apparatus 34 is removed from the right atrium and, typically, from the body of the subject. Guidewire 60 remains in the left atrium at this step of the procedure. For some applications, such as shown in FIG. 1F, needle 32 (and dilator element 49, if provided) are proximally withdrawn from the right atrium, while catheter 38 is left in the right atrium for use at left-side therapeutic delivery step 166, described hereinbelow. For other applications (not shown), catheter 38 is also withdrawn from the right atrium, and a separate catheter is introduced for performing left-side therapeutic delivery step 166.

At a left-side therapeutic delivery step 166, a left-side therapeutic delivery system 74 is introduced (i.e., advanced) over guidewire 60, through the hole in the fossa ovalis, and into the left atrium, as shown in FIG. 1G. For example, left-side therapeutic delivery system 74 may comprise a delivery tool (e.g., comprising one or more tubes), and a valve repair or replacement device or a left atrial appendage implant. Left-side therapeutic delivery system 74 is introduced through catheter 38, if catheter 38 has been left in the right atrium, or through another catheter, if catheter 38 has been withdrawn from the right atrium.

Figure 11A:
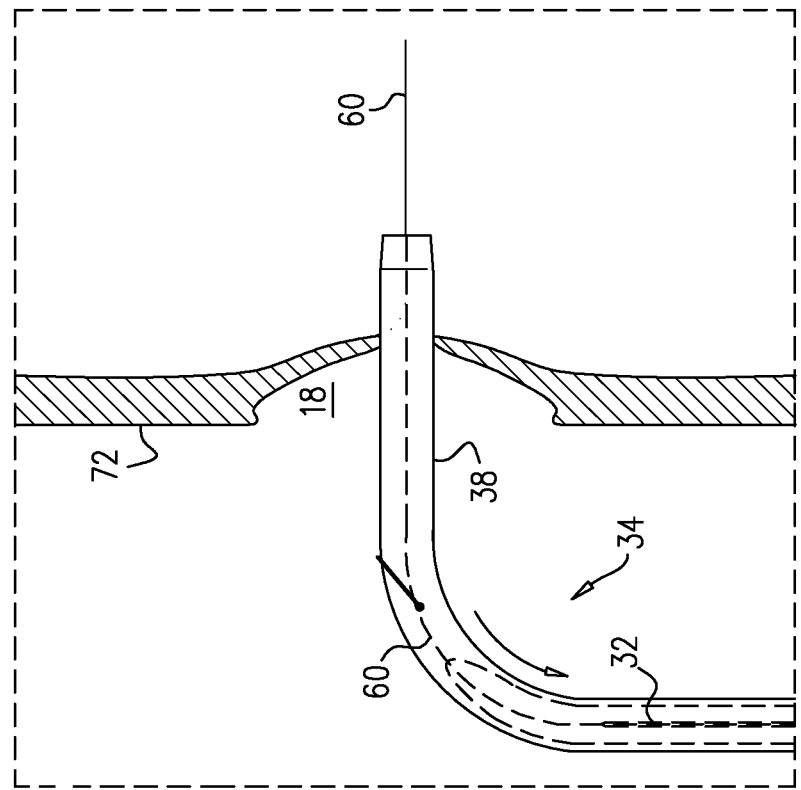
FIGS. 11A-B are schematic illustrations of an alternative method for delivering a left-side therapeutic delivery system to the left side of the heart, in accordance with an application of the present invention.
Figure 11B:
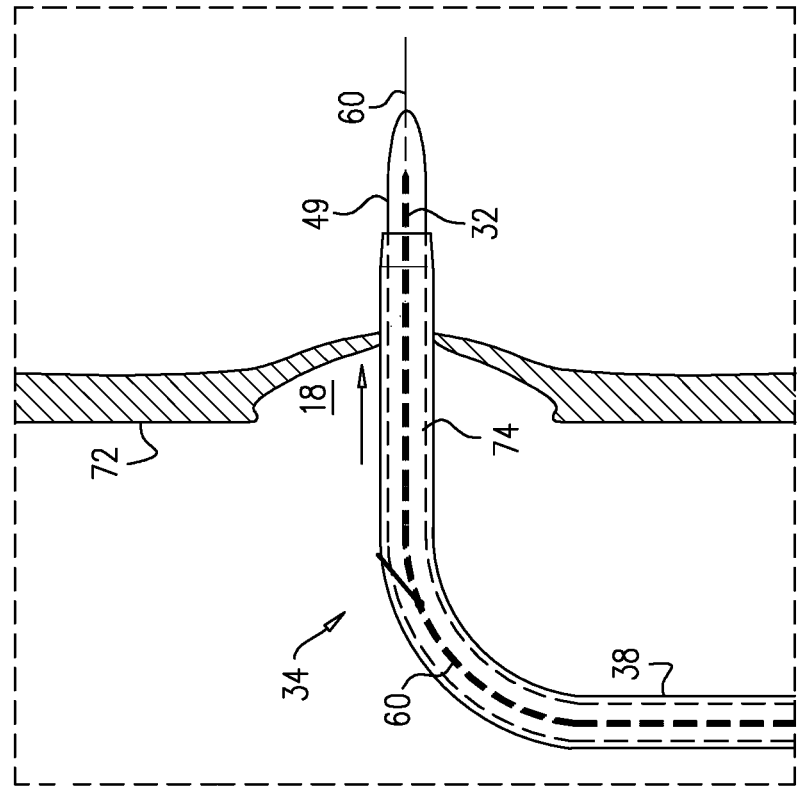

Reference is now made to FIGS. 11A-B, which are schematic illustrations of an alternative method for delivering left-side therapeutic delivery system 74 to the left side of the heart, in accordance with an application of the present invention. In this alternative method, after dilator element 49 has been advanced into the left atrium, as described hereinabove with reference to FIG. 1E, catheter 38 is further advanced distally through the dilated hole in the fossa ovalis and into the left atrium, as shown in FIG. 11A. At apparatus removal step 164, as shown in FIG. 11B, needle 32 and dilator element 49 are removed from the right atrium, while catheter 38 and guidewire 60 are left in the left atrium for use at left-side therapeutic delivery step 166. Alternatively, guidewire 60 is also withdrawn at apparatus removal step 164, and is thus not used at left-side therapeutic delivery step 166.

Figure 12:
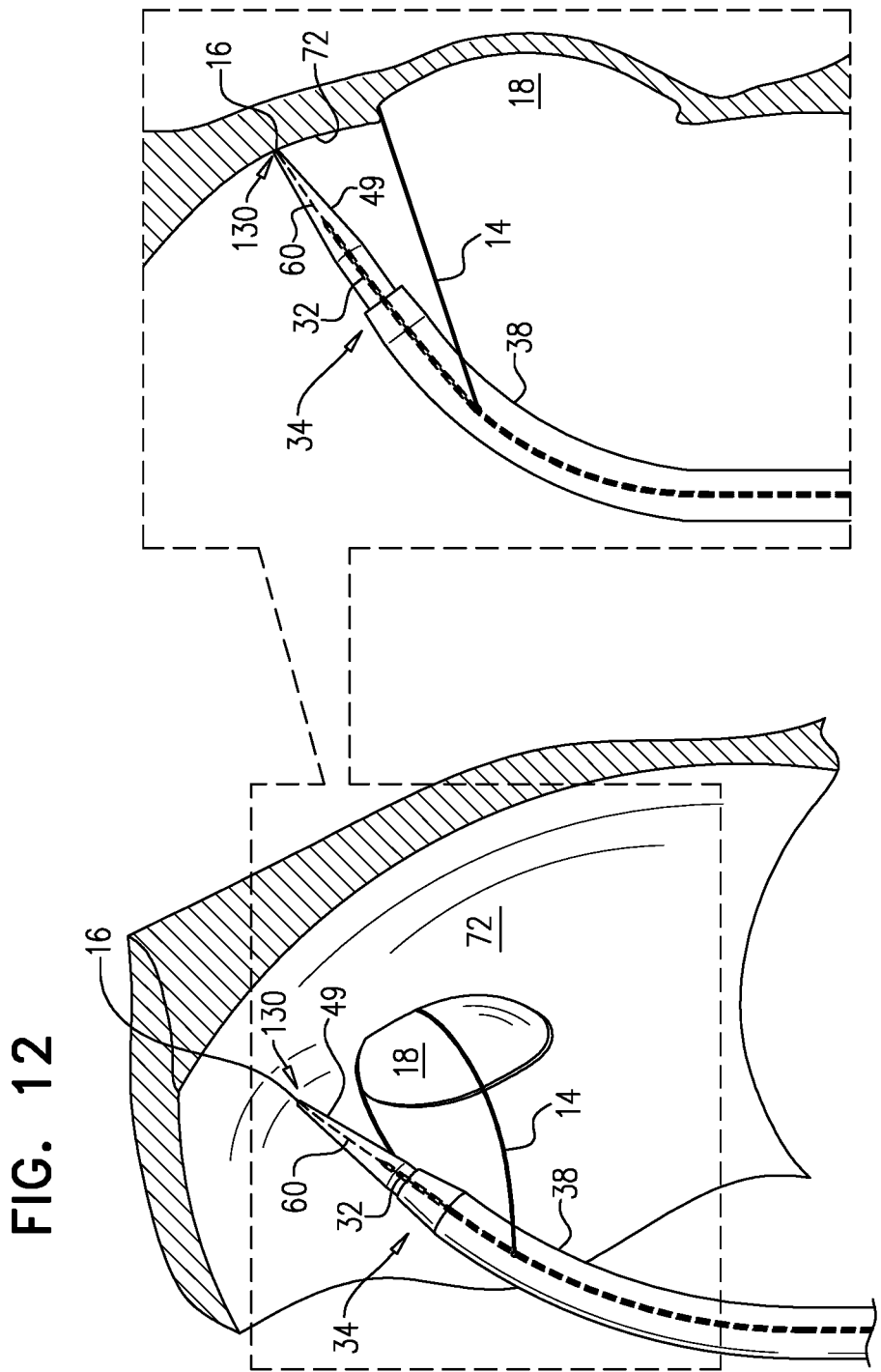
FIG. 12 is a schematic illustration of an alternative method of using the apparatus described herein, in accordance with an application of the present invention.

Reference is now made to FIG. 12, which is a schematic illustration of an alternative method of using apparatus 34, in accordance with an application of the present invention. Other than as described below, this method is similar to the method shown in FIGS. 1B-C, and may be performed in combination with any of the apparatus and methods described herein. This method may be performed with or without the techniques described herein of partially withdrawing guidewire 60.

In this method, the loop-shaped deployed portion of flexible longitudinal member 14 has been deployed against fossa ovalis 18 (e.g., against an inner perimeter of the fossa ovalis), as described hereinabove with reference to FIGS. 1B-C. Dilator tip 16 is then brought in contact with a site 130 on a surface of interatrial septum 72 outside fossa ovalis 18. Following the contacting, needle 32 is deployed, typically while within dilator element 49, by being advanced through a distal opening of the dilator tip, and through interatrial septum 72 at site 130, thus puncturing a hole in the interatrial septum. Alternatively or additionally, the hole is created using energy applied with the needle, rather than force-based mechanical puncturing by the needle, as described hereinbelow with reference to FIG. 15. Dilator tip 16 then dilates an opening created by the needle. Alternatively, such as if dilator element 49 is not provided, a distal end of needle 32 is brought directly in contact with site 130. Alternatively, site 130 is located on a wall of the right atrium other than on interatrial septum 72.

For some applications, site 130 is disposed superior to fossa ovalis 18, such as shown in FIG. 12. Alternatively, site 130 is disposed in another direction from fossa ovalis 18, such as inferior and/or lateral to fossa ovalis 18.

For some applications, such as if site 130 is disposed superior to fossa ovalis 18, such as shown in FIG. 12, the distal end of needle 32 is not passed through the deployed portion of flexible longitudinal member 14 to a second side of the deployed portion of flexible longitudinal member 14 (unlike in the configuration described hereinabove with reference to FIG. 1C). For other applications, such as if site 130 is disposed inferior to fossa ovalis 18 (not shown) or the direction from catheter 38 of deployment of flexible longitudinal member 14 is different from that shown, the distal end of needle 32 is passed through the deployed portion of flexible longitudinal member 14 to a second side of the deployed portion of flexible longitudinal member 14 (similar to the configuration described hereinabove with reference to FIG. 1C).

Reference is still made to FIG. 12. In accordance with some applications of the present invention, a method is provided for puncturing interatrial septum 72, the method comprising inserting catheter 38 into the right atrium, and advancing a distal portion of the catheter toward fossa ovalis 18. Flexible longitudinal member 14 is deployed from catheter 38, such that a deployed portion of flexible longitudinal member 14 is loop-shaped. Fossa ovalis 18 (e.g., an inner perimeter of the fossa ovalis) is contacted with the deployed portion of flexible longitudinal member 14. Needle 32 is deployed from catheter 38 (either before, after, or simultaneously with deployment of flexible longitudinal member 14 from the catheter). A distal end of the needle is brought in contact with site 130 on a surface of interatrial septum 72 outside fossa ovalis 18, and interatrial septum 72 is punctured at site 130 with needle 32. The deployed portion of flexible longitudinal member 14 is withdrawn toward catheter 38.

For some applications, the method further comprises, before contacting fossa ovalis 18 with the deployed portion of flexible longitudinal member 14, moving the deployed portion of the flexible longitudinal member along the surface of interatrial septum 72, until the flexible longitudinal member contacts the fossa ovalis. For some applications, moving the deployed portion of the flexible longitudinal member along the surface of the interatrial septum comprises moving the deployed portion of the flexible longitudinal member toward the fossa ovalis from below the fossa ovalis.

For some applications, deploying the flexible longitudinal member comprises deploying the flexible longitudinal member such that a deployment angle of the flexible longitudinal member is between 10 and 80 degrees, the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point, such as described hereinabove with reference to FIG. 1C. For some applications, deploying the flexible longitudinal member comprises deploying the flexible longitudinal member such that the deployment angle is between 30 and 60 degrees.

For some applications, deploying the flexible longitudinal member from the catheter comprises passing the flexible longitudinal member through two lateral openings at a distal portion of the catheter.

For some applications, the flexible longitudinal member is radiopaque, and wherein the method further comprises using fluoroscopic imaging to view the flexible longitudinal member during and after deployment thereof.

For some applications, the method further comprises, before puncturing the fossa ovalis, flexing a distal portion of the needle by steering the catheter.

Figure 13:
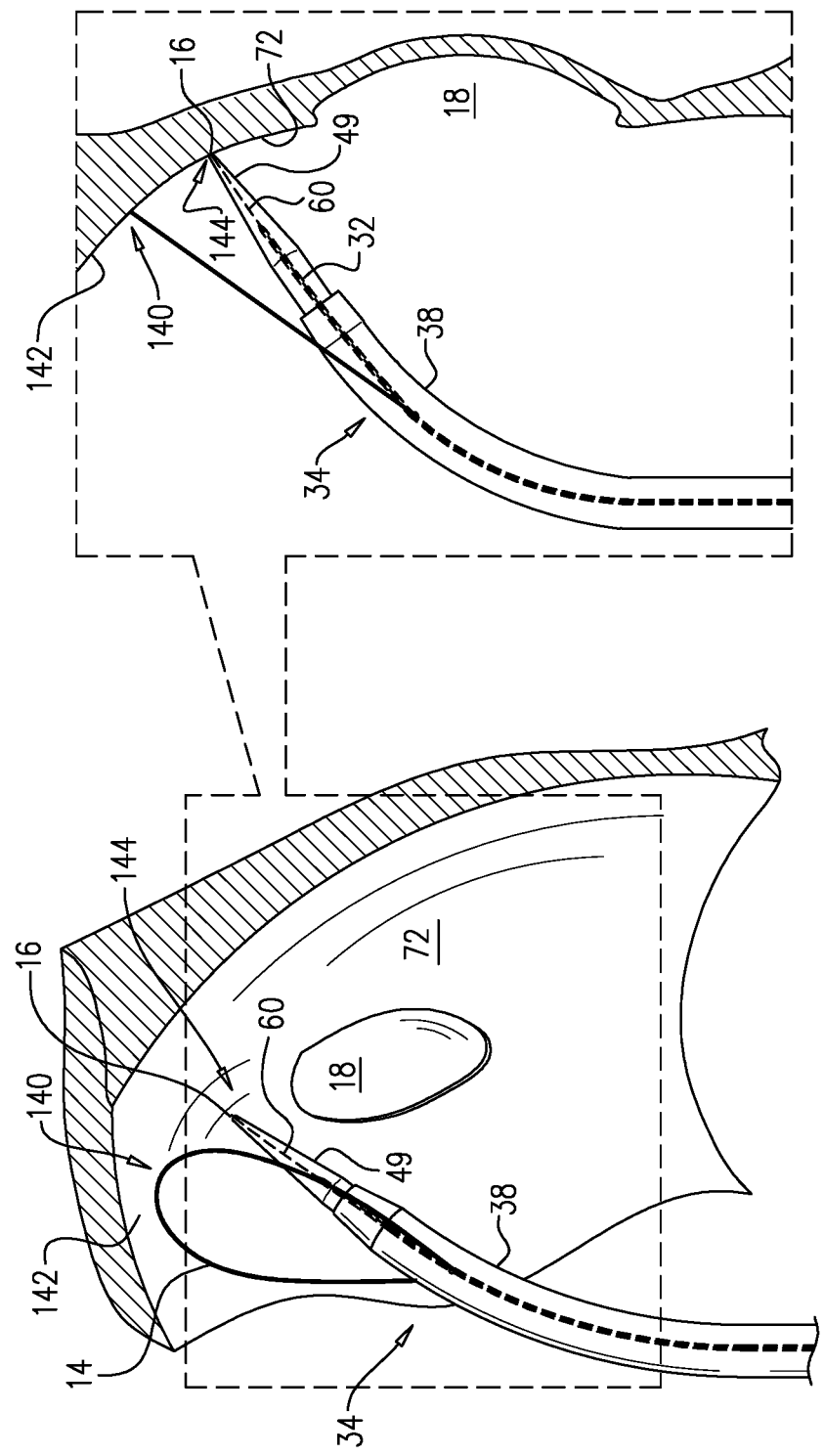
FIG. 13 is a schematic illustration of an alternative method of using the apparatus described herein, in accordance with an application of the present invention.

Reference is now made to FIG. 13, which is a schematic illustration of an alternative method of using apparatus 34, in accordance with an application of the present invention. Other than as described below, this method is similar to the method shown in FIGS. 1B-C, and may be performed in combination with any of the apparatus and methods described herein. This method may be performed with or without the techniques described herein of partially withdrawing guidewire 60.

In this method, the loop-shaped deployed portion of flexible longitudinal member 14 is deployed against a surface of the right atrium other than fossa ovalis 18, such as against a stabilization site 140 located (a) on a roof 142 of the right atrium, (b) at the junction between roof 142 and interatrial septum 72, or (c) on interatrial septum 72 superior to fossa ovalis 18, in order to stabilize catheter 38 (the opening of the superior vena cava is avoided). Dilator tip 16 is then brought in contact with a hole site 144 on a surface of interatrial septum 72 outside fossa ovalis 18. Following the contacting, needle 32 is deployed, typically while within dilator element 49, by being advanced through a distal opening of the dilator tip, and through interatrial septum 72 at hole site 144, thus puncturing a hole in the interatrial septum. Alternatively or additionally, the hole is created using energy applied with the needle, rather than force-based mechanical puncturing by the needle, as described hereinbelow with reference to FIG. 15. Dilator tip 16 then dilates an opening created by the needle. Alternatively, such as if dilator element 49 is not provided, a distal end of needle 32 is brought directly in contact with hole site 144. Alternatively, hole site 144 is located on a wall of the right atrium other than on interatrial septum 72.

Typically, hole site 144 is disposed superior to fossa ovalis 18, such as shown in FIG. 13. Alternatively, hole site 144 is disposed in another direction from fossa ovalis 18, such as inferior and/or lateral to fossa ovalis 18.

Depending on the direction of deployment from catheter 38 of flexible longitudinal member 14, the distal end of needle 32 may be passed through the deployed portion of flexible longitudinal member 14 to a second side of the deployed portion of flexible longitudinal member 14 (as described hereinabove with reference to FIG. 1C), or may not be passed through the deployed portion.

For some other applications, such as if apparatus 34 is introduced into the right atrium from the superior vena cava, stabilization site 140 is located (a) on an annulus of the tricuspid valve, (b) at the junction between the annulus and interatrial septum 72, or (c) on interatrial septum 72 inferior to fossa ovalis 18, in order to the stabilize catheter 38.

Reference is still made to FIG. 13. In accordance with some applications of the present invention, a method is provided for puncturing interatrial septum 72, the method comprising inserting catheter 38 into the right atrium, and advancing a distal portion of the catheter toward roof 142 of the right atrium. Flexible longitudinal member 14 is deployed from catheter 38, such that a deployed portion of flexible longitudinal member 14 is loop-shaped. Stabilization site 140 is contacted with the deployed portion of flexible longitudinal member 14, stabilization site 140 being located (a) on roof 142 of the right atrium, (b) between roof 142 and interatrial septum 72, or (c) on interatrial septum 72 superior to fossa ovalis 18. Needle 32 is deployed from catheter 38 (either before, after, or simultaneously with deployment of flexible longitudinal member 14 from the catheter). A distal end of needle 32 is brought in contact with hole site 144 on a surface of interatrial septum 72, and interatrial septum 72 is punctured at hole site 144 with needle 32. The deployed portion of flexible longitudinal member 14 is withdrawn toward catheter 38.

For some applications, deploying flexible longitudinal member 14 from catheter 38 comprises passing flexible longitudinal member 14 through two lateral openings at a distal portion of the catheter.

For some applications, the flexible longitudinal member is radiopaque, and wherein the method further comprises using fluoroscopic imaging to view the flexible longitudinal member during and after deployment thereof.

For some applications, the method further comprises, before puncturing the interatrial septum, flexing a distal portion of the needle by steering the catheter.

Figure 14:
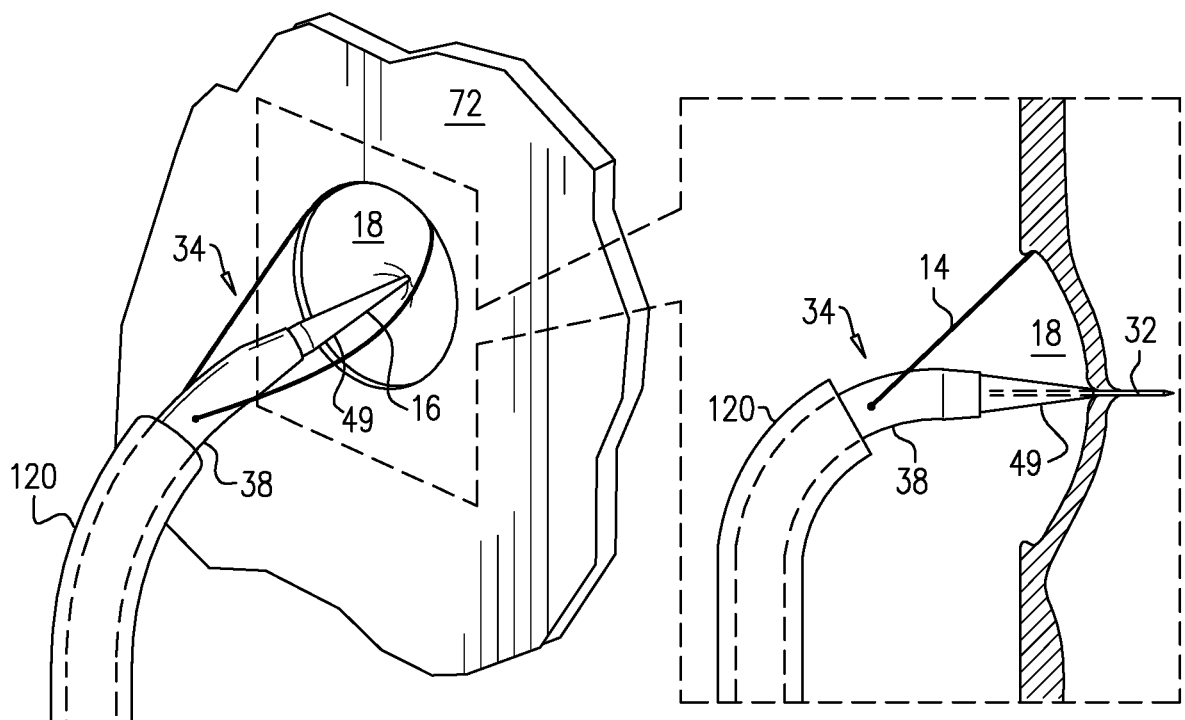
FIG. 14 is a schematic illustration of the use of the apparatus described herein in combination with a left-side therapeutic delivery system, in accordance with an application of the present invention.

Reference is made to FIG. 14, which is a schematic illustration of the use of apparatus 34 in combination with a left-side therapeutic delivery system, in accordance with an application of the present invention. This technique may be practiced in combination with any of the techniques described herein. In this application, a delivery catheter 120 of a left-side therapeutic delivery system is first inserted into the right atrium, using techniques known in the art. Apparatus 34, including catheter 38 thereof, is advanced through delivery catheter 120 into the right atrium, and is then used to puncture fossa ovalis 18 or another site on interatrial septum 72, using techniques described herein. Thereafter, apparatus 34 is withdrawn from the body through delivery catheter 120, leaving delivery catheter 120 in the heart. Delivery catheter 120 is used to introduce a left-side therapeutic device, such as a valve repair or replacement device or a left atrial appendage implant.

Typically, an outer diameter of delivery catheter 120 equals at least 150% of an outer diameter of catheter 38, such as at least 200%. For example, the outer diameter of delivery catheter 120 may be between 20 and 30 Fr, and the outer diameter of catheter 38 may be between 12 and 14 Fr.

For some applications, before withdrawal of apparatus 34 from the body, delivery catheter 120 is advanced over dilator element 49 while the dilator element is disposed within the hole in fossa ovalis 18 or the other site on interatrial septum 72, until a distal end opening of delivery catheter 120 is disposed in the left atrium. After withdrawal of apparatus 34 from the body, delivery catheter 120 is used to introduce the left-side therapeutic device into the left atrium.

Figure 15:
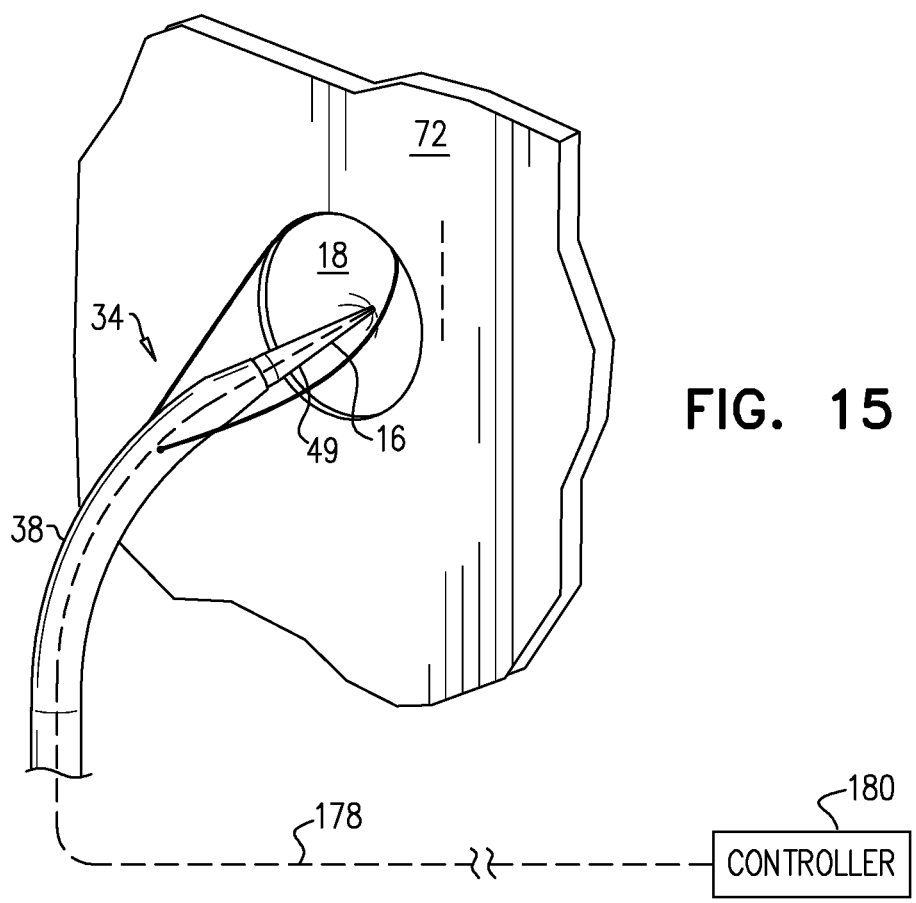
FIG. 15 is a schematic illustration of a configuration of the apparatus described herein, in accordance with an application of the present invention.

Reference is made to FIG. 15, which is a schematic illustration of a configuration of apparatus 34, in accordance with an application of the present invention. This technique may be practiced in combination with any of the techniques described herein. In this application, needle 32 is electrically conductive, and is coupled by one or more conductors 178 to a controller 180, which comprises or is in electrical communication with an energy source. The controller is configured to drive needle 32 to apply an ablating current, e.g., an RF current, to puncture the fossa ovalis or interatrial septum 72. Alternatively, instead of using an ablating current, other energy may be applied, such as heat, ultrasound, or light (e.g., laser) energy. The energy-based puncturing may be performed instead of or in combination with the force-based mechanical puncturing by the needle. For some applications, the distal tip of the needle is blunt.

Figure 16:
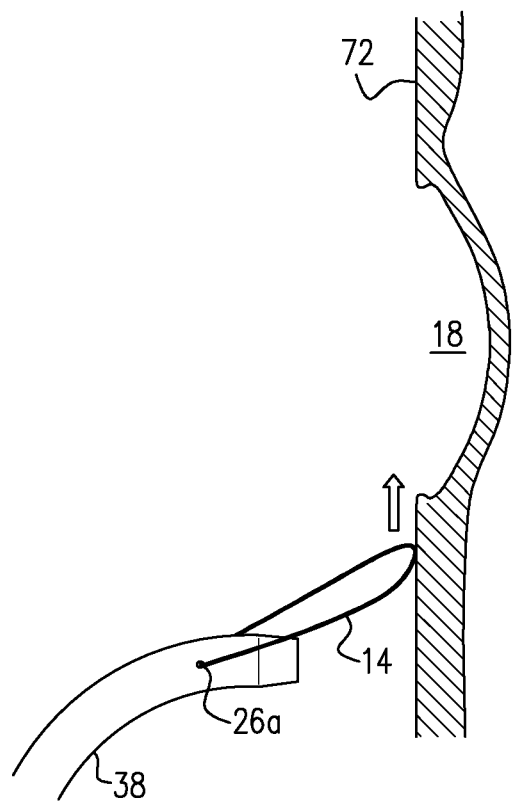
FIG. 16 is a schematic illustration of a method for puncturing the fossa ovalis, in accordance with some applications of the present invention.

Reference is now made to FIG. 16, which is a schematic illustration of a method for puncturing the fossa ovalis, in accordance with some applications of the present invention. Before contacting the fossa ovalis with the deployed portion of flexible longitudinal member 14, the deployed portion of the flexible longitudinal member is moved along a surface of interatrial septum 72, until the flexible longitudinal member contacts the fossa ovalis. In some applications, as shown in FIG. 16, the deployed portion of the flexible longitudinal member is moved toward the fossa ovalis from below the fossa ovalis. In some applications, the flexible longitudinal member is radiopaque and/or is coupled to a plurality of radiopaque markers. In such applications, fluoroscopic imaging is used to view the flexible longitudinal member during and after deployment thereof. For example, fluoroscopic imaging may be used to view the flexible longitudinal member as it is moved toward the fossa ovalis, in order to help identify when the flexible longitudinal member has reached the fossa ovalis.

Reference is now made to FIGS. 17-18, which are schematic illustrations of catheter 38, in accordance with some applications of the present invention. FIG. 17 shows a control element 30 (e.g., a control handle) shaped to surround a proximal portion of catheter 38. Control element 30 facilitates the steering of the catheter, as well as control of needle 32 and/or of flexible longitudinal member 14. As described hereinabove with reference to FIGS. 2A-B, wall 39 of catheter 38 typically comprises braided portion 41 and unbraided portion 43. Typically, control element 30 surrounds the catheter such that (a) all of the catheter wall that is distal to a distal end of the control element comprises braided portion 41, and (b) at least 10% of the catheter wall that is proximal to the distal end of the control element comprises unbraided portion 43. Typically, a length L1 of the braided portion is between 600 and 1000 mm, and/or a length L2 of the unbraided portion is between 250 and 400 mm.

Typically, a braided wall is preferred to an unbraided wall, because the braiding reduces the buckling of the catheter when a pushing force is applied. However, some manufacturing processes limit the number of lateral openings that can be made through a braided wall; thus, in order to allow for the proximal lateral openings 84 shown in FIG. 18, it may be necessary, when using such manufacturing processes, to make the proximal portion of the catheter wall unbraided. Some applications of the present invention compensate for the use of an unbraided wall, by including a reinforcing tube 82 that at least partially surrounds the unbraided portion of the catheter wall. Reinforcing tube 82 provides stability to the catheter, in lieu of the braiding. As shown in FIG. 18, a wall of the reinforcing tube is typically shaped to define one or more lateral openings 84 therethrough. (Openings 84 are aligned with lateral openings in the catheter wall.) Control wires 80, and/or flexible longitudinal member 14, pass through openings 84 into channels 20, 27a, and 27b, shown in FIGS. 2A-B. Control element 30 is coupled to control wires 80, and/or to flexible longitudinal member 14.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Provisional Application 61/811,947, filed Apr. 15, 2013;

U.S. application Ser. No. 14/245,135, filed Apr. 4, 2014, which published as US Patent Application Publication 2014/0309675;

International Application PCT/IL2014/050338, filed Apr. 7, 2014, which published as PCT Publication WO 2014/170890;

U.S. application Ser. No. 14/287,470, filed May 27, 2014, which published as US Patent Application Publication 2014/0309678;

U.S. application Ser. No. 14/287,523, filed May 27, 2014, which published as US Patent Application Publication 2014/0309679;

U.S. application Ser. No. 14/513,435, filed Oct. 14, 2014, which published as US Patent Application Publication 2016/0100859;

U.S. Provisional Application 62/095,150, filed Dec. 22, 2014; and

U.S. application Ser. No. 14/636,759, filed Mar. 3, 2015; and

PCT Application PCT/IL2015/051026, filed on Oct. 14, 2015, entitled, "Fossa ovalis penetration," which published as WO 2016/059638.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   inserting a catheter into a right atrium of a heart of the subject;
   advancing a distal portion of the catheter toward a fossa ovalis of the heart;
   deploying a flexible longitudinal member from the catheter, such that a deployed portion of the flexible longitudinal member is made to loop around and against a portion of an inner perimeter of the fossa ovalis;
   deploying a needle from the catheter;
   while the flexible longitudinal member is looped around and against the portion of the inside perimeter of the fossa ovalis, bringing a distal end of the needle in contact with a site on a surface of an interatrial septum of the heart outside the fossa ovalis;
   forming a hole through the interatrial septum at the site with the needle; and
   withdrawing the deployed portion of the flexible longitudinal member toward the catheter.

2. The method according to claim 1, wherein the forming of the hole through the interatrial septum comprises puncturing the interatrial septum with a sharp distal tip of the needle.

3. The method according to claim 1, wherein the forming of the hole through the interatrial septum comprises applying energy to the interatrial septum with the needle.

4. The method according to claim 1, further comprising, before the contacting of the fossa ovalis with the deployed portion of the flexible longitudinal member, moving the deployed portion of the flexible longitudinal member along the surface of the interatrial septum, until the flexible longitudinal member contacts the fossa ovalis.

5. The method according to claim 4, wherein the moving of the deployed portion of the flexible longitudinal member along the surface of the interatrial septum comprises moving the deployed portion of the flexible longitudinal member toward the fossa ovalis from below the fossa ovalis.

6. The method according to claim 1, wherein the deploying of the flexible longitudinal member comprises deploying the flexible longitudinal member such that a deployment angle of the flexible longitudinal member is between 10 and 80 degrees,
   the deployment angle being an angle between (a) a vector that is (i) tangent to the flexible longitudinal member at an exit point of the flexible longitudinal member from the catheter, and (ii) directed away from the catheter, and (b) a distally-directed vector that is parallel to a longitudinal axis of the catheter at the exit point.

7. The method according to claim 6, wherein the deploying of the flexible longitudinal member comprises deploying the flexible longitudinal member such that the deployment angle is between 30 and 60 degrees.

8. The method according to claim 1, wherein the deploying of the flexible longitudinal member from the catheter comprises passing the flexible longitudinal member through two lateral openings at a distal portion of the catheter.

9. The method according to claim 1, wherein the flexible longitudinal member is radiopaque, and wherein the method further comprises using fluoroscopic imaging to view the flexible longitudinal member during and after deployment thereof.

10. The method according to claim 1, further comprising, before the forming of the hole through the interatrial septum, flexing a distal portion of the needle by steering the catheter.

11. The method according to claim 1, wherein the catheter is a puncture-tool catheter, and wherein the inserting of the catheter into the right atrium comprises:
   inserting a delivery catheter of a left-side therapeutic delivery system into the right atrium; and
   advancing the puncture-tool catheter through the delivery catheter into the right atrium.

* * * * *